US009474569B2

(12) United States Patent
Manzo et al.

(10) Patent No.: US 9,474,569 B2
(45) Date of Patent: *Oct. 25, 2016

(54) SURGICAL INSTRUMENT WITH END EFFECTOR COMPRISING JAW MECHANISM AND TRANSLATING COMPONENT, AND RELATED METHODS

(71) Applicant: INTUITIVE SURGICAL OPERATIONS, INC., Sunnyvale, CA (US)

(72) Inventors: Scott E. Manzo, Shelton, CT (US); Lawrence Kerver, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/718,944

(22) Filed: May 21, 2015

(65) Prior Publication Data

US 2015/0250530 A1    Sep. 10, 2015

Related U.S. Application Data

(63) Continuation of application No. 13/399,391, filed on Feb. 17, 2012, now Pat. No. 9,055,961.

(60) Provisional application No. 61/444,400, filed on Feb. 18, 2011, provisional application No. 61/491,719, filed on May 31, 2011.

(51) Int. Cl.
*A61B 18/14* (2006.01)
*A61B 17/00* (2006.01)
*A61B 18/00* (2006.01)

(52) U.S. Cl.
CPC ....... *A61B 18/1445* (2013.01); *A61B 18/1482* (2013.01); *A61B 34/30* (2016.02);
(Continued)

(58) Field of Classification Search
CPC .......... A61B 18/1445; A61B 18/1482; A61B 19/2203; A61B 2017/00477; A61B 2018/00083; A61B 2018/00607; A61B 2018/0063; A61B 2018/00982; A61B 2018/1452; A61B 2018/1455; A61B 2019/2238; A61B 2019/2242
See application file for complete search history.

(56) References Cited

U.S. PATENT DOCUMENTS

| 5,752,973 A | 5/1998 | Kieturakis |
| 5,792,135 A | 8/1998 | Madhani et al. |

(Continued)

FOREIGN PATENT DOCUMENTS

| CN | 1726874 A | 2/2006 |
| CN | 101181167 A | 5/2008 |

(Continued)

OTHER PUBLICATIONS

Second Office Action for related Chinese Application No. 201280005049.5 entitled "Fusing and Cutting Surgical Instrument and Related Methods," dated Nov. 24, 2015.

(Continued)

*Primary Examiner* — Scott Getzow

(57) ABSTRACT

A surgical instrument can include a shaft having a proximal end and a distal end, and a wrist coupled to the distal end of the shaft and configured to articulate in multiple degrees of freedom. An end effector having jaws may be supported by the wrist. The surgical instrument can further include a first drive element extending from the proximal end of the shaft to the end effector, the first drive element being configured to transmit forces to move the jaws relative to each other between open and closed positions, and a second drive element extending from the proximal end of the shaft to the end effector, the second drive element being configured to transmit forces to translate a component of the end effector in a longitudinal direction relative to the jaws. The component can be configured to translate independently of movement of the jaws.

27 Claims, 13 Drawing Sheets

(52) U.S. Cl.
CPC .... *A61B 34/71* (2016.02); *A61B 2017/00477* (2013.01); *A61B 2018/0063* (2013.01); *A61B 2018/00083* (2013.01); *A61B 2018/00607* (2013.01); *A61B 2018/00982* (2013.01); *A61B 2018/1452* (2013.01); *A61B 2018/1455* (2013.01); *A61B 2034/306* (2016.02)

(56) References Cited

U.S. PATENT DOCUMENTS

| | | | |
|---|---|---|---|
| 5,848,986 | A | 12/1998 | Lundquist et al. |
| 6,817,974 | B2 | 11/2004 | Cooper et al. |
| 7,799,028 | B2 | 9/2010 | Schechter et al. |
| 7,861,906 | B2 | 1/2011 | Doll et al. |
| 7,918,230 | B2 | 4/2011 | Whitman et al. |
| 8,579,176 | B2 | 11/2013 | Smith et al. |
| 9,055,961 | B2 | 6/2015 | Manzo et al. |
| 2002/0099371 | A1 | 7/2002 | Schulze et al. |
| 2002/0177842 | A1 | 11/2002 | Weiss |
| 2003/0125734 | A1 | 7/2003 | Mollenauer |
| 2003/0208186 | A1 | 11/2003 | Moreyra |
| 2006/0022015 | A1 | 2/2006 | Shelton et al. |
| 2006/0025811 | A1 | 2/2006 | Shelton, IV |
| 2007/0233052 | A1 | 10/2007 | Brock |
| 2008/0015631 | A1 | 1/2008 | Lee et al. |
| 2010/0274265 | A1 | 10/2010 | Wingardner et al. |
| 2010/0292691 | A1 | 11/2010 | Brogna |
| 2011/0118707 | A1 | 5/2011 | Burbank |
| 2011/0118708 | A1 | 5/2011 | Burbank et al. |
| 2011/0118709 | A1 | 5/2011 | Burbank |
| 2011/0118754 | A1 | 5/2011 | Dachs, II et al. |

FOREIGN PATENT DOCUMENTS

| | | |
|---|---|---|
| CN | 101500498 A | 8/2009 |
| JP | 2000102545 A | 4/2000 |
| JP | 2006034978 A | 2/2006 |
| JP | 2008036219 A | 2/2008 |
| JP | 2011504794 A | 2/2011 |
| WO | WO-9743942 A1 | 11/1997 |
| WO | WO-2004052171 A2 | 6/2004 |
| WO | WO-2010015798 A1 | 2/2010 |

OTHER PUBLICATIONS

International Search Report and Written Opinion for Application No. PCT/US2012/025644, mailed on Aug. 20, 2012, 16 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

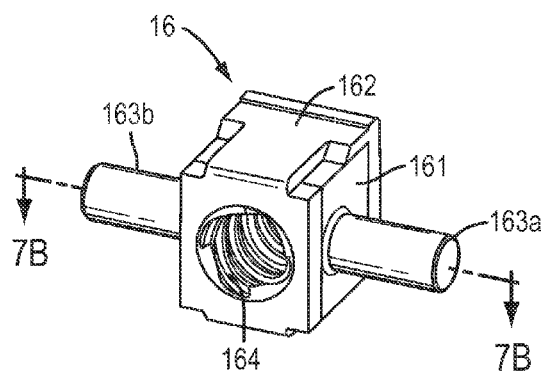
FIG. 7A
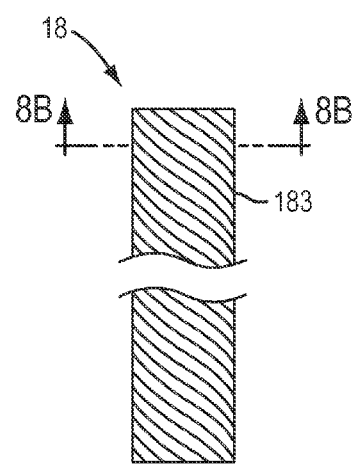
FIG. 8A
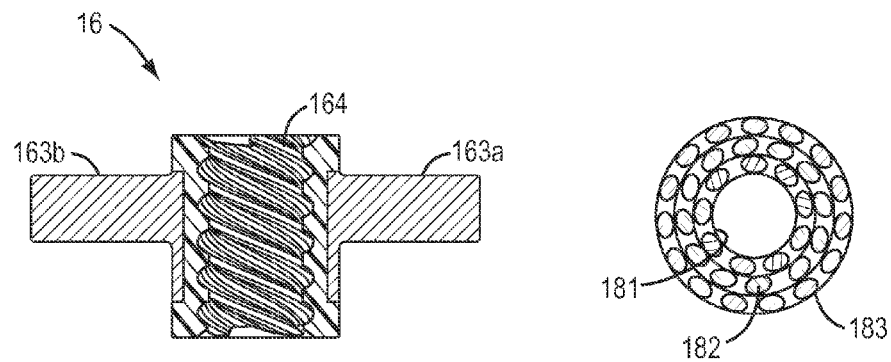
FIG. 7B
FIG. 8B

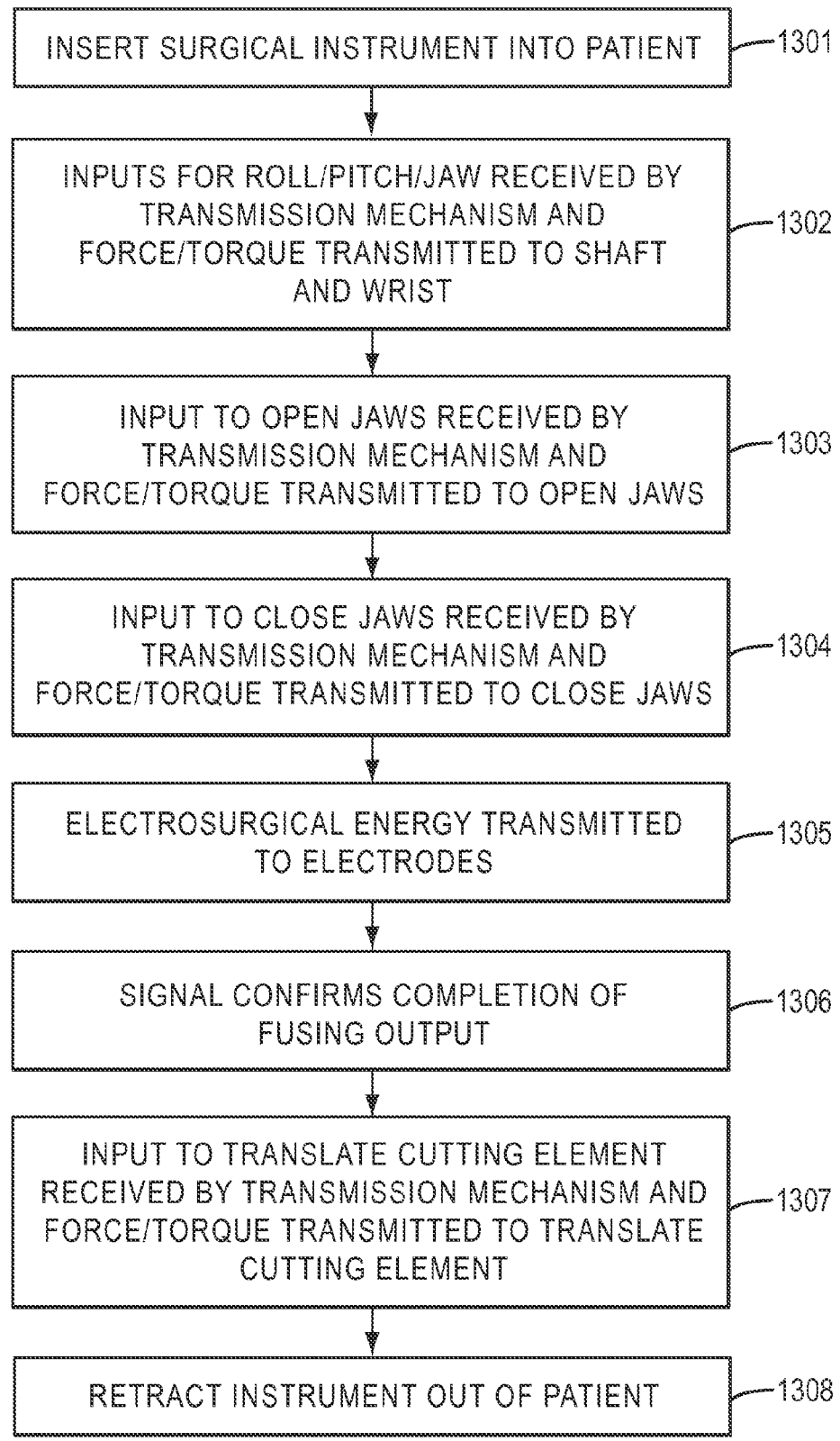

SURGICAL INSTRUMENT WITH END EFFECTOR COMPRISING JAW MECHANISM AND TRANSLATING COMPONENT, AND RELATED METHODS

CROSS-REFERENCE TO RELATED APPLICATIONS

This application claims priority to U.S. patent application Ser. No. 13/399,391, filed Feb. 17, 2012 (now pending), which claims the benefit of U.S. Provisional Patent Application No. 61/444,400, filed on Feb. 18, 2011, and to U.S. Provisional Patent Application No. 61/491,719, filed May 31, 2011, the entire content of each of which is incorporated by reference herein.

TECHNICAL FIELD

Aspects of the present disclosure relate to surgical instruments that are minimally invasive and integrate into a single device the use of energy to fuse tissue and a component that cuts the fused tissue. More particularly, aspects of the present disclosure relate to such devices that have an articulating wrist mechanism that supports a surgical instrument end effector configured to cut and fuse tissue.

INTRODUCTION

The use of energy, such as, for example bipolar energy, to fuse tissue is known. Briefly, two or more tissues (e.g., a tissue bundle) are gripped between two electrodes, and electrosurgical energy is passed between the electrodes in order to fuse the tissues together. An example of such tissues includes the opposing walls of a blood vessel. In this way, the blood vessel can be fused closed, resulting in a sealing of the vessel at the fused region. Surgical instruments that perform this action are often referred to as sealing instruments (e.g., a "vessel sealer"). Such surgical instruments also can be used, for example, for cold cutting, tissue dissection, coagulation of tissue bundles generally (e.g., other than for sealing), and tissue manipulation/retraction.

Once tissues, such as, for example, of a blood vessel, are fused together, the fused region can be safely cut without any resulting bleeding. For both convenience and cutting accuracy, surgical instruments have been developed that utilize an end effector that integrates the use of tissue fusing and cutting.

The benefits of minimally invasive (e.g., laparoscopic, thoracoscopic, etc.) surgery are known. Instruments for such surgery typically have a surgical end effector mounted at the distal end of a long shaft that is inserted through an opening (e.g., body wall incision, natural orifice) to reach a surgical site. In some cases, the surgical instruments can be passed through a cannula and an endoscope can be used to provide images of the surgical site. In some cases, an articulating wrist mechanism may be mounted at the instrument's distal end to support the end effector and change its orientation with reference to the shaft's longitudinal axis. It can be appreciated that minimizing the outer diameter of the shaft, wrist, and end effector may be desirable to reduce patient trauma during minimally invasive surgery.

A disadvantage of existing minimally invasive surgical instruments that offer an integrated tissue fusing and cutting end effector is that the articulating wrist mechanism allows the end effector to articulate relative to the shaft with only a single degree of freedom (DOF) (e.g., arbitrarily defined orthogonal "pitch" or "yaw" orientations with reference to the shaft), although other DOF movements may be considered to exist, such as, for example, roll, grip, translation (e.g., movement of cutting knife along the jaws), etc. This single articulation DOF limitation is due to the configuration of the cutting knife, which is typically an elongated, substantially planar metal band or ribbon structure having a distal end provided with sharp cutting edges. Such a planar structure can flex back and forth about the plane in which the structure lies, but not in the orthogonal plane (i.e., in the plane of the structure). Since the planar cutting knife structure passes through the wrist mechanism in order to drive the cutting knife, the wrist mechanism is limited to a configuration in which only a single articulation DOF motion can occur, namely about the plane of the planar cutting knife; the wrist mechanism is not configured to articulate within the plane of the planar cutting knife structure. Cutting knives with planar band or ribbon structures can also impact the roll DOF of a surgical instrument, requiring various coupling structures to maintain substantially concentric positioning between the various elements of the end effector during roll.

Attaining sufficient gripping pressure on tissue, such as a vessel, for sealing can also be challenging in such instruments, particularly when combined with achieving various other DOF movements, such as, for example, roll DOF and articulation DOF. Also, attaining sufficient gripping pressure can pose challenges when attempting to reduce the size of the overall instrument.

Another type of minimally invasive surgical instrument is a stapling instrument. Such stapling instruments securely staple tissues together with several staple rows, and these instruments also use an integrated cutting mechanism to drive a cutting knife between the staple rows. Minimally invasive stapling instruments with a tissue cutting feature have been developed with the integrated stapling and cutting end effector mounted on a two-DOF articulation wrist mechanism so that the end effector orientation can be changed in both "pitch" and "yaw". See e.g., U.S. patent application Ser. No. 12/945,461 (filed Nov. 12, 2010; disclosing motor interface for parallel drive shafts within an independently rotating member), U.S. patent application Ser. No. 12/945,730 (filed Nov. 12, 2010; disclosing wrist articulation by linked tension members), U.S. patent application Ser. No. 12/945,740 (filed Nov. 12, 2010; disclosing double universal joint), and U.S. patent application Ser. No. 12/945,748 (filed Nov. 12, 2010; disclosing surgical tool with a two degree of freedom wrist). But such instruments with two-DOF articulation wrist mechanisms typically have an outer diameter of the wrist and end effector (i.e., stapler) that is larger than many other minimally invasive surgical instruments. In one instance, for example, a two-DOF articulation wrist stapler has an outer diameter of about 13 mm. In one instance, a stapling device has been modified to perform a tissue fusing and sealing function, and because of its structure has an outer diameter similar to a stapling instrument. See, e.g., U.S. Patent Application Pub. No. US 2010/0292691 A1 (filed Jul. 22, 2010). In contrast, other minimally invasive surgical instruments, such as those used with the robotic surgical systems commercialized by Intuitive Surgical, Inc. of Sunnyvale, Calif., have an outer diameter of the wrist and/or end effector (e.g., in a closed position of jaws of the end effector) in the range of about 8 mm or about 5 mm.

Persons of ordinary skill in the art will appreciate that reducing the overall size of a surgical instrument while preserving desired functions, features, and capabilities is often not merely a case of scaling down known components. Preserving design requirements for even a small size reduction, such as reducing an instrument's outer diameter by about 2 mm to about 3 mm, can be a difficult task due to material properties, component fabrication limitations, introduction of friction between moving parts, limitations on strength of components as their sizes are reduced, overall design of such smaller mechanisms while maintaining high force requirements, and other impacts on operation. Thus, although highly desirable, a minimally invasive surgical instrument with an integrated tissue fusing and cutting feature, a two-DOF articulation wrist mechanism, and an outer diameter on the order of other commonly used minimally invasive surgical instruments has not been available. In addition, such a surgical instrument that can be interfaced with and controlled by a robotic surgical system is desirable.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments, the present teachings contemplate a surgical instrument that comprises a shaft having a proximal end and a distal end, and a wrist coupled to the distal end of the shaft and configured to articulate in multiple degrees of freedom coupled to the distal end of the shaft. The surgical instrument can further comprise an end effector supported by the wrist, wherein the end effector includes a cutting element and jaws configured to grip tissue and to fuse tissue, for example, via electrosurgical energy. The surgical instrument can be configured for use with a teleoperated robotic surgical system that can include a patient side console configured to interface with and actuate the surgical instrument and a surgeon side console configured to receive inputs from a surgeon to control the actuation of the surgical instrument.

In accordance with various exemplary embodiments, the present teachings contemplate a method of operating a surgical instrument which includes receiving at least one first input at a transmission mechanism disposed at a proximal portion of the surgical instrument to articulate a multiple degree-of-freedom articulable wrist of the surgical instrument in at least one of pitch and yaw, and transmitting one or more forces via the transmission mechanism to articulate the wrist in response to the first input. The method further includes receiving a second input at the transmission mechanism to open jaws of an end effector supported by the wrist, and transmitting torque via the transmission mechanism to a torque drive component to open the jaws. The method further includes receiving a third input at the transmission mechanism to close the jaws of the end effector, and transmitting torque via the transmission mechanism to the torque drive component to close the jaws to grip tissue between the jaws. Additionally, the method includes transmitting electrosurgical energy to the jaws to fuse the tissue, receiving a fourth input at the transmission mechanism to translate a cutting element of the end effector, and transmitting a force to a cutting element drive component via the transmission mechanism to translate the cutting element relative to the end effector.

Additional objects and advantages of the present teachings will be set forth in part in the description which follows, and in part will be obvious from the description, or may be learned by practice of the present disclosure and/or claims. At least some of those objects and advantages of the invention will be realized and attained by means of the elements and combinations particularly pointed out in the appended claims.

It is to be understood that both the foregoing general description and the following detailed description are exemplary and explanatory only and are not restrictive of the present disclosure and claims, which are entitled to their full breadth of scope including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

FIG. 7A is a perspective view of a grip drive nut in accordance with an exemplary embodiment;

FIG. 7B is a cross-sectional view of the grip drive nut taken from the perspective 7B-7B in FIG. 7A;

FIG. 8A is a partial side view of an exemplary embodiment of a torque tube in accordance with an exemplary embodiment;

FIG. 8B is a cross-sectional view of the torque tube from the perspective 8B-8B of FIG. 8A;

FIG. 13 is a flow diagram showing an exemplary method for operating a fusing and cutting surgical instrument in accordance with various exemplary embodiments of the present disclosure;

DETAILED DESCRIPTION

Figure 1:
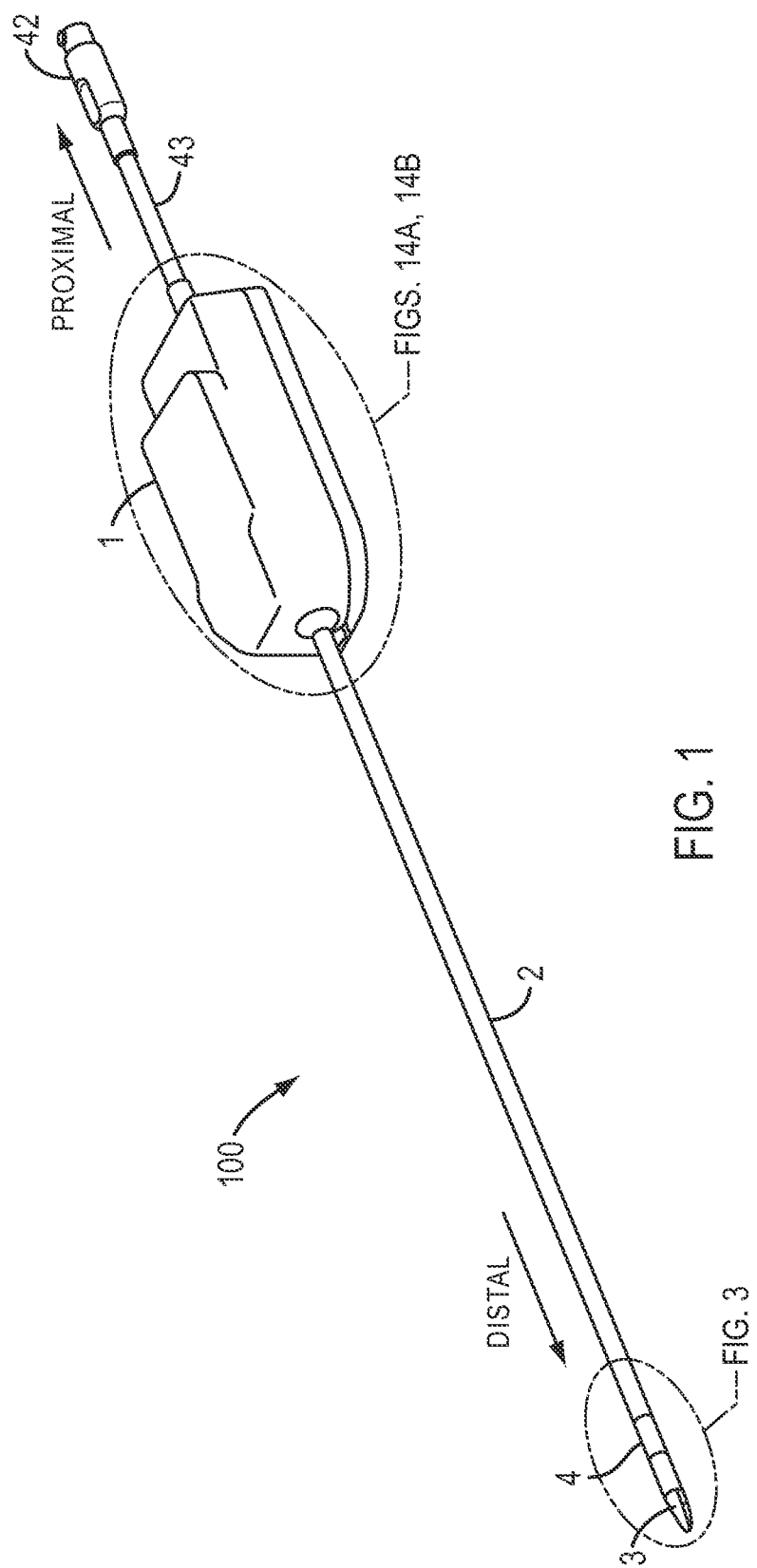
FIG. 1 is a diagrammatic perspective view of a minimally invasive surgical instrument in accordance with an exemplary embodiment of the present disclosure.

This description and the accompanying drawings that illustrate exemplary embodiments should not be taken as limiting, with the claims defining the scope of the present disclosure. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates a surgical instrument that includes a shaft, a wrist that is capable of articulating in both pitch and yaw directions and combinations thereof, and an end effector that includes components operable to perform gripping, fusing, and cutting procedures. The present disclosure contemplates such a surgical instrument that is able to provide both a sufficient gripping force (including pressure on the gripped tissue) desirable for achieving tissue (e.g., vessel) fusing and a sufficient cutting force, throughout a relatively wide range of articulation and roll DOF movements of the instrument. Further, in various exemplary embodiments, the present disclosure contemplates such a surgical instrument that is minimally invasive, and provides a compact design, having overall outer diameters of the shaft, wrist, and end effector that are relatively small in comparison with other minimally invasive surgical instruments that use articulation wrist structures in combination with multiple purpose end effectors, such as various stapling instruments for example.

Various exemplary embodiments of the present disclosure thus provide an integrated tissue fusing and cutting end effector, the orientation of which can be independently controlled in Cartesian pitch, yaw, and roll DOFs. In addition, the cutting element can be independently controlled in translation DOF for movement relative to the end effector substantially along a longitudinal direction of the end effector jaws, even when the wrist is articulated in pitch and/or yaw relative to a longitudinal axis of the instrument shaft, and/or when the instrument shaft and end effector are rolled (i.e., rotated about the longitudinal axis of the shaft).

Figure 14A:
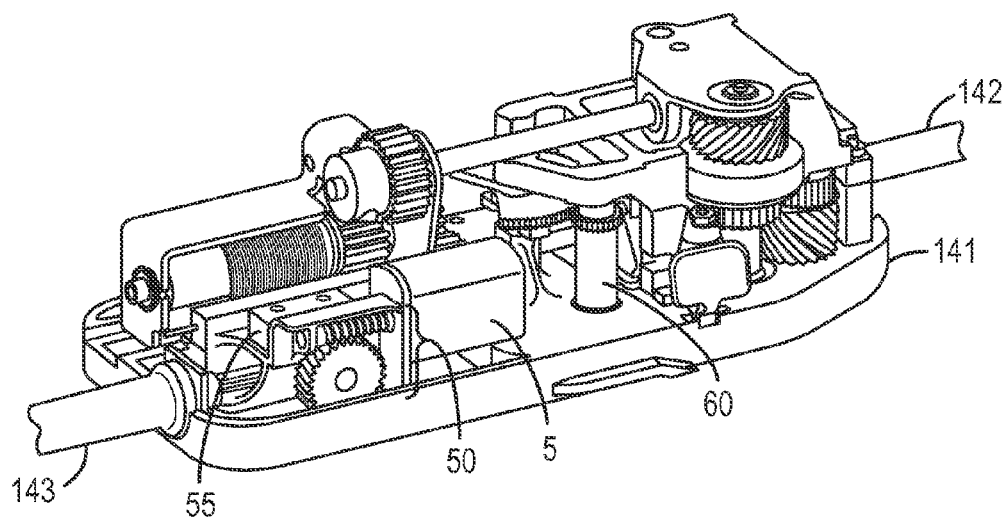
FIGS. 14A-14B are detailed views of the corresponding labeled portions of the surgical instrument of FIG. 1 in accordance with an exemplary embodiment.
Figure 14B:
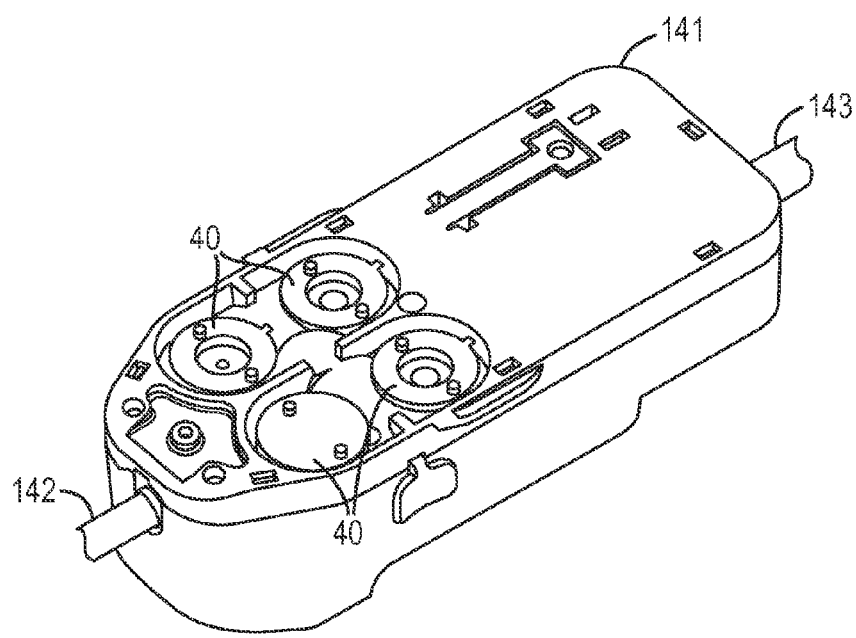

With reference now to FIG. 1, a diagrammatic view of a minimally invasive surgical instrument 100, and various components thereof shown in detail, in accordance with an exemplary embodiment of the present disclosure is depicted. FIG. 1 is a perspective view of the minimally invasive surgical instrument 100, and FIGS. 14A-14B show the detailed views of an exemplary embodiment of the corresponding portion labeled in FIG. 1. The directions "proximal" and "distal" are used herein to define the directions as shown in FIG. 1, with distal generally being in a direction further along a kinematic arm or closest to the surgical work site in the intended operational use of the instrument 100, for example, in use for performing surgical procedures. As shown in FIG. 1, the instrument 100 generally includes a force/torque drive transmission mechanism 1, an instrument shaft 2 mounted to the transmission mechanism 1; an integrated gripping, fusing, and cutting end effector 3 disposed at the distal end of the instrument 100; and an articulation wrist 4 disposed at a distal end of the shaft 2 between the shaft 2 and the end effector 3. In various exemplary embodiments, the overall length of the instrument 100 from the distal end of the end effector 3 to the proximal end of the transmission mechanism 1 ranges from about 21 inches to about 25 inches.

Figure 12A:
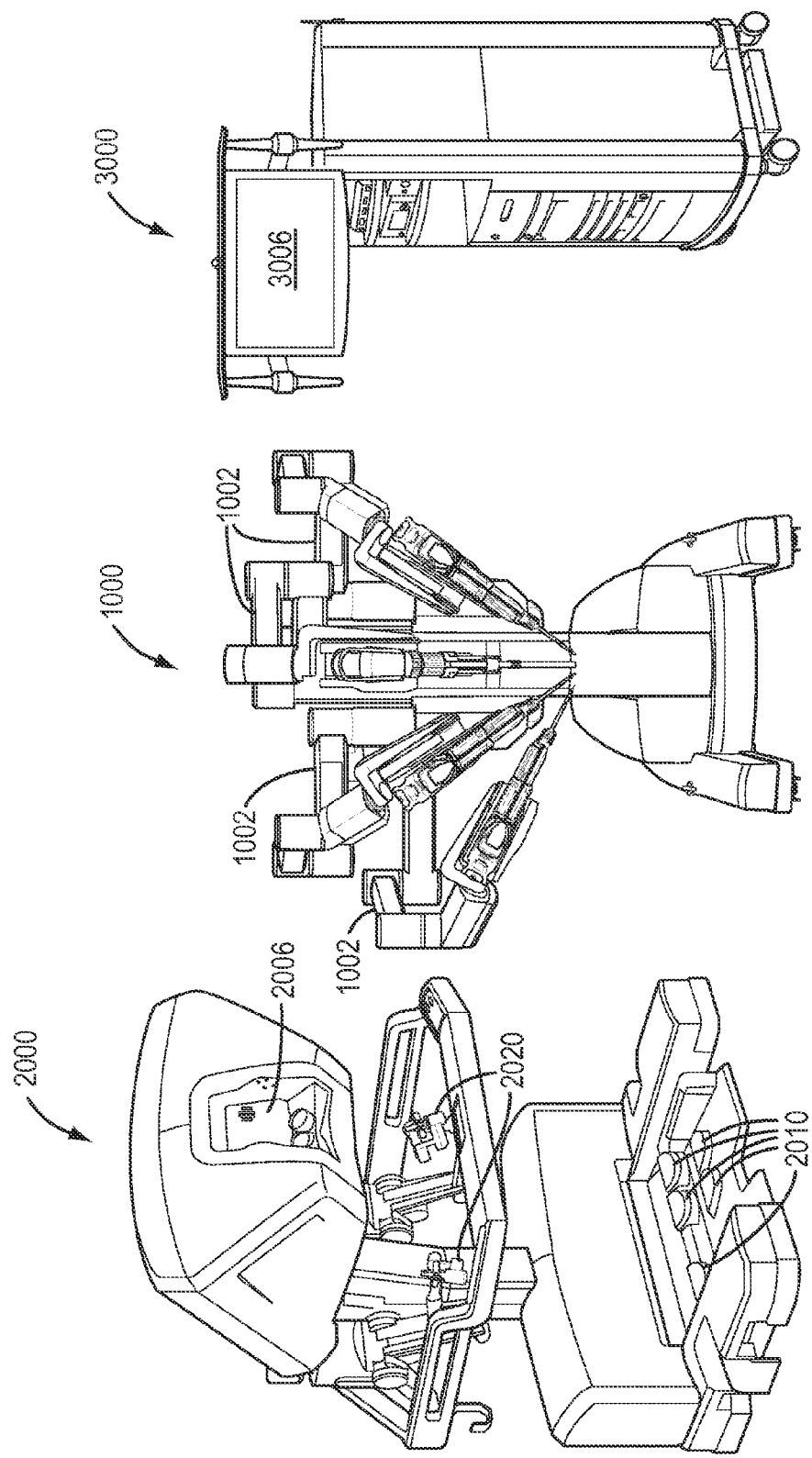
FIG. 12A is a diagrammatic perspective view of an exemplary robotic surgical system with which surgical instruments in accordance with various exemplary embodiments of the present disclosure can be used.
Figure 12B:
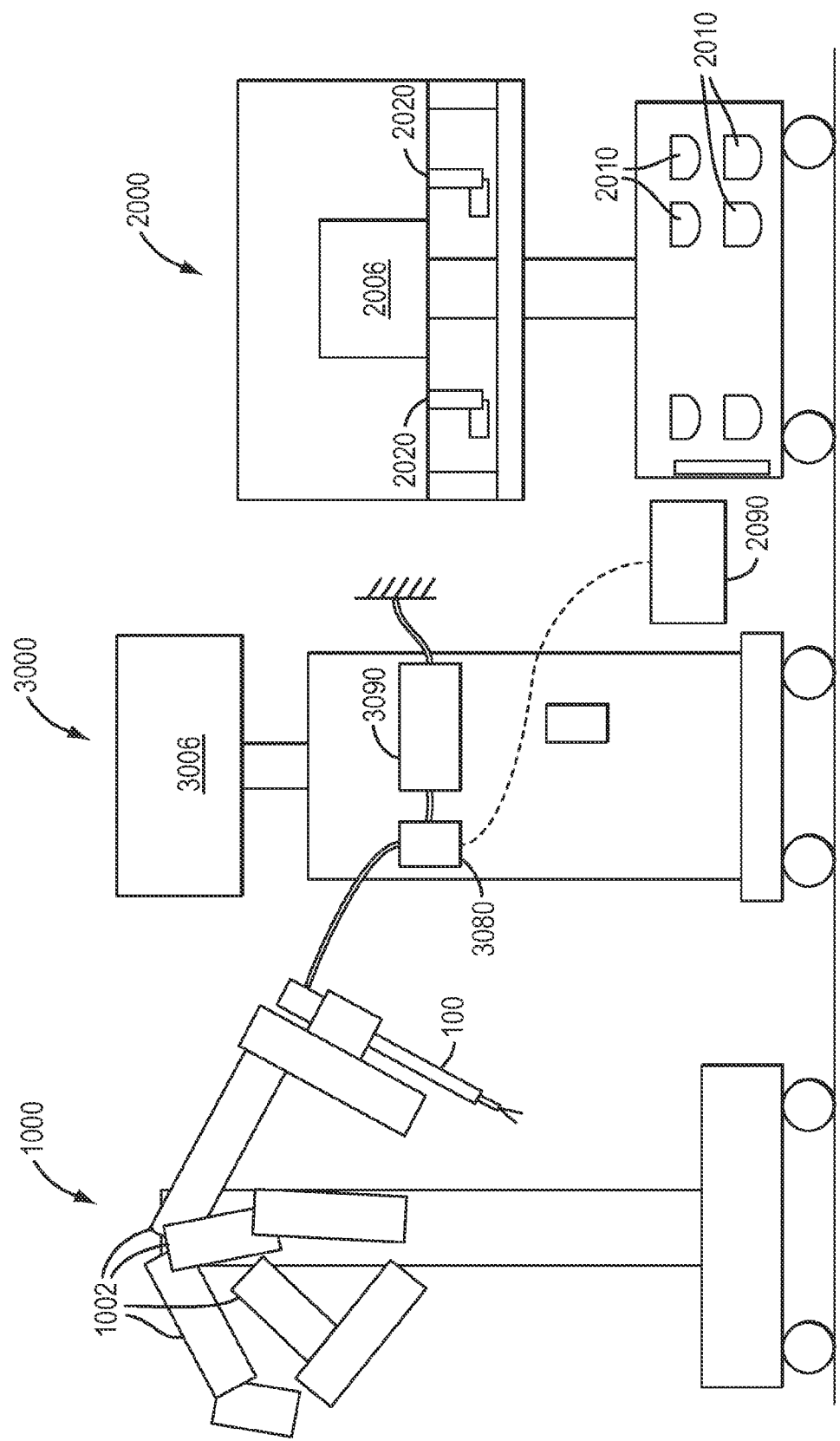
FIG. 12B is a schematic view of an exemplary robotic surgical system with which surgical instruments in accordance with various exemplary embodiments of the present disclosure can be used.

In an exemplary embodiment, the instrument 100 is configured to be mounted on and used with a minimally invasive surgical robotic system, which in an exemplary embodiment includes a patient side console 1000, a surgeon side console 2000, and an electronics/control console 3000, as illustrated in the diagrammatic perspective and schematic views of FIGS. 12A and 12B. It is noted that the system components in FIGS. 12A and 12B are not shown in any particular positioning and can be arranged as desired, with the patient side console being disposed relative to the patient so as to effect surgery on the patient. A non-limiting, exemplary embodiment of a surgical robotic system with which the instrument 100 can be utilized is a da Vinci® Si (model no. IS3000) commercialized by Intuitive Surgical, Inc. In general, the surgeon side console 2000 receives inputs from a surgeon by various input devices, including but not limited to, gripping mechanisms 2004, foot pedals 2002, etc. The surgeon side console serves as a master controller by which the patient side console 1000 acts as a slave to implement the desired motions of the surgical instrument, and accordingly perform the desired surgical procedure. The surgeon side console 2000 also can include a viewer or display 2006 that allows the surgeon to view a three dimensional image of the surgical site. The patient side console 1000 can include a plurality of jointed arms 1002 configured to hold various tools, including, but not limited to, for example, a surgical instrument with an end effector (e.g., surgical instrument 100), and an endoscope. Based on the commands input at the surgeon side console 2000, the patient side console 1000 can interface with a transmission mechanism of the surgical instrument to position and actuate the instrument to perform a desired medical procedure. The electronics/control console 3000 receives and transmits various control signals to and from the patient side console 1000 and the surgeon side console 2000, and can transmit light and process images (e.g., from an endoscope at the patient side console 1000) for display, such as, e.g., display 2006 at the surgeon side console 2000 and/or on a display 3006 associated with the electronics/control console 3000. Those having ordinary skill in the art are generally familiar with such robotically controlled surgical systems.

In an exemplary embodiment, the electronics/control console 3000 may have all control functions integrated in one or more controllers in the console 3000, or additional controllers (e.g., as shown at 3080 in FIG. 12B) may be provided as separate units and supported (e.g., in shelves) on the electronics/control console 3000 for convenience. Such controllers may, in exemplary embodiments, be in direct electrical/control communication with a surgical instrument 100, as shown, e.g., by in FIG. 12B. The latter may be useful, for example, when retrofitting existing electronics/control consoles to control surgical instruments requiring additional functionality. The electronics/control console 3000 also can include a separate controller 3090 for electrocautery energy in an exemplary embodiment, which can be delivered to the surgical instrument end effector. Likewise, although in various exemplary embodiments, one or more input mechanisms may be integrated into the surgeon side console 2000, various other input mechanisms (e.g., as shown by element 2090 in FIG. 12B) may be added separately and provided so as to be accessible to the surgeon during use of the system, but not necessarily integrated into the surgeon side console 2000.

The transmission mechanism 1 transmits received actuation inputs to resulting torques and forces to effect movement of the instrument shaft 2, wrist 4, and end effector 3, and associated components, to accomplish various motions resulting in a multi-DOF surgical instrument. For example, the transmission mechanism 1 can be controlled via inputs (e.g., torque inputs) to roll shaft 2, and consequently end effector 3 (roll DOF); open and close jaws of the end effector 3 (grip or clamp DOF); articulate wrist 4 (articulation DOF); and translate a cutting element (not shown in the view of FIG. 1) (translation DOF). In various exemplary embodiments, as will be described in further detail below, the wrist 4 can be configured for two-DOF articulation in orthogonal directions to provide both "pitch" and "yaw" movement of end effector 3 (yaw being arbitrarily defined as being the plane of motion of the end effector jaws, pitch being orthogonal to yaw).

As depicted in the exemplary embodiment of FIG. 14B, which shows the underside of an exemplary embodiment of a transmission mechanism 141 that can be used as transmission mechanism 1 in FIG. 1, the transmission mechanism 141 can include one or more input drive disks 40 configured to interface with a patient-side control console, such as console 1000 in FIGS. 12A and 12B, to receive input to drive the various motions of the instrument 1, as will be explained in more detail below.

As mentioned above, in an exemplary embodiment, for example as shown in FIGS. 14A and 14B, the transmission mechanism 141 (shown in FIG. 14A with its protective cover removed to provide an internal view) can be configured to receive various inputs, including for example, torque inputs via teleoperated servo actuators of a robotic surgical system that interface with the input disks 40, as persons with ordinary skilled in the art are familiar with. These torque inputs can be used to transmit roll to the instrument shaft (labeled 142 in FIGS. 14A and 14B), to transmit a force to open and close the jaws of the end effector (FIG. 1 shows the jaws of end effector 3 in a closed position), and to transmit a force to articulate the wrist (wrist 4 in FIG. 1), for example, two-DOF articulation. In addition, in an exemplary embodiment, the transmission mechanism 141 can include an onboard electric motor 5 that receives input voltages, for example from a robotic surgical control system (e.g., via a controller that is either integrated into central control console 3000 or separate therefrom but associated therewith), to drive the cutting element (not shown in FIG. 1) via gears and a rack and pinion mechanism 50. For further details regarding driving and controlling the cutting element using an onboard motor like onboard motor 5, reference is made to U.S. Provisional Patent Application No. 61/491,698, entitled "SURGICAL INSTRUMENT WITH MOTOR" (filed May 31, 2011), and to U.S. Provisional Patent Application No. U.S. 61/491,671, entitled "SURGICAL INSTRUMENT WITH CONTROL FOR DETECTED FAULT CONDITION" (filed May 31, 2011), both of which are incorporated by reference in their entireties herein.

Although the exemplary embodiment of FIGS. 14A and 14B depicts a transmission mechanism 141 configured to interface and receive drive torque/force input from a robotic surgical system that includes teleoperated servo actuators, in alternative embodiments a transmission mechanism that relies on additional onboard motors and/or manual actuation could be utilized with the surgical instrument of FIG. 1. Persons of ordinary skill in the art will understand that depending on the number of actuation inputs available, some instrument embodiments may receive all actuation inputs from outside the instrument (e.g., from teleoperated servo motors), some (e.g., hand held instruments) may have onboard motors to drive all the instrument features, and some, such as the depicted embodiment of that incorporates the transmission mechanism depicted in FIGS. 14A and 14B, may have various combinations of external actuation inputs and onboard drive motors. In the case of onboard motors, the input voltage used to drive such motors can be supplied from a central controller (e.g., such as electronics/ control console 3000 and/or associated separately mounted controllers (e.g., controller 3080), as depicted in FIGS. 12A and 12B) or from voltage sources provided on the instrument itself in the case of handheld instruments. Likewise, persons having ordinary skill in the art will understand that various combinations of gears, pulleys, links, gimbal plates, and/or levers, etc. (exemplary embodiments of which are depicted in FIG. 14A) can be used to transmit actuating forces and torques to various instrument components. For further details regarding exemplary components that may be used in the transmission mechanism 1, 141 to convert the inputs, received for example via a patient side console 1000 in FIGS. 12A and 12B, to the transmission mechanism 1, 141 to torques and/or forces to ultimately drive the motions of the shaft 2, jaws of the end effector 3, and wrist 4, reference is made to U.S. Provisional Patent Application No. U.S. 61/491,804, entitled "GRIP FORCE CONTROL IN A ROBOTIC SURGICAL INSTRUMENT" (filed May 31, 2011); U.S. Provisional Patent Application No. U.S. 61/491, 798 and U.S. patent application Ser. No. U.S. 13/297,168, both entitled "DECOUPLING INSTRUMENT SHAFT ROLL AND END EFFECTOR ACTUATION IN A SURGICAL INSTRUMENT" (filed May 31, 2011 and Nov. 15 2011, respectively); and U.S. Provisional Application No. U.S. 61/491,821, entitled "SURGICAL INSTRUMENT WITH SINGLE DRIVE INPUT FOR TWO END EFFECTOR MECHANISMS" (filed May 31, 2011), all of which are incorporated by reference in their entireties herein.

The transmission mechanism 1, 141 also can accommodate electrical conductors (not shown in FIG. 1 or FIGS. 14A and 14B) to receive electrosurgical energy via connector 42, 142 that is ultimately transmitted to the end effector 3 and used to fuse tissue. The electrical conductors can be routed through a protective tube 43, 143 from the transmission mechanism 1, 141.

Figure 2:
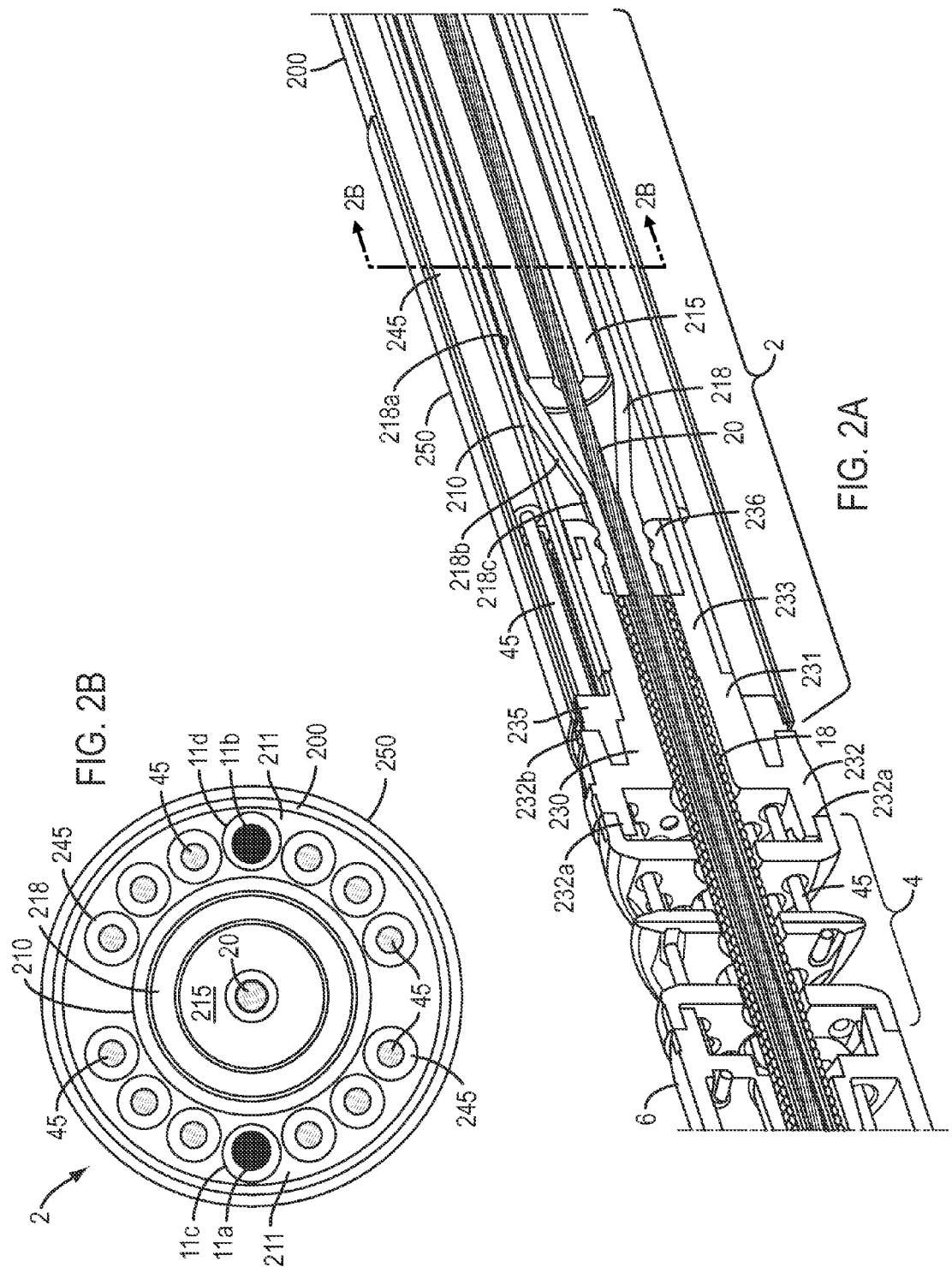
FIG. 2A is a partial, longitudinal cross-sectional view of a shaft and wrist of the surgical instrument of FIG. 1 in accordance with an exemplary embodiment.
FIG. 2B is a transverse, cross-sectional view of the instrument shaft taken from the perspective 2B-2B in FIG. 2A.

With reference now to the cross-sectional views of FIGS. 2A and 2B, shaft 2 is substantially rigid and comprises a main tube 200 surrounded by an insulation layer 250. In various exemplary embodiments, the main tube 200 can be made of a material exhibiting high tensile strength metal with relatively thin wall thicknesses, such as, for example, stainless steel. The ability to provide a relatively strong, yet thin walled tube permits strength requirements to be met while also maximizing the internal space through which various components of the instrument can pass. In various exemplary embodiments, the outer insulation layer can be electrically insulative and comprise a material that exhibits relatively high dielectric strength and relatively high scratch resistance, can be relatively easily applied to the tube 200, has relatively low friction, and/or has a relatively low dielectric constant. In one exemplary embodiment, the outer insulation layer may be an epoxy coating, such as, for example, a multi-layer (e.g., two-layer) epoxy coating. Other suitable materials for the outer insulation layer can include, but are not limited to, for example, polyvinylidene fluoride (PVDF), polyolefin, and/or fluoroethylene-propylene (FEP).

The main tube 200 is configured for routing various components from the transmission mechanism 1 to the wrist 4 and end effector 3 (not shown in FIGS. 2A and 2B). A center channel 210 provides a lumen that receives both an end effector grip hollow drive shaft 218, which is coupled to a torque drive component 18 routed through wrist 4, and an end effector cutting element drive component 20, both of which are described in more detail below. Disposed in the space between and concentrically with the cutting element drive component 20 and the interior surface of the drive shaft 218 is a spacer mechanism 215. The spacer mechanism 215 helps to position the cutting element drive component 20 and to absorb forces during operation of the instrument that tend to buckle the cutting element drive component 20. In various exemplary embodiments, the spacer mechanism 215 can be made of a plastic that has relatively low friction, such as, for example, low-density polyethylene (LDPE) or other suitable materials. The hollow drive shaft 218 includes a region 218a of larger inner and outer diameters, a region 218c of smaller inner and outer diameters, and a transition region 218b where the inner and outer diameters taper from the region 218a to the region 218c. More specifically, the region 218a has an outer diameter that is approximately equal to the inner diameter of the center channel 210 and an inner diameter that is sufficient to accommodate the spacer mechanism 215. The region 218c has an inner diameter that is approximately equal to the outer diameter of the cutting element drive component 20 and an outer diameter that is substantially equal to the outer diameter of the torque drive component 18. The larger diameter region 218a assists to minimize twisting forces on the tube 218 resulting from forces associated with a torque drive component 18 (explained in further detail below) used to open and close the jaws of the end effector. The smaller diameter region 218c permits the drive shaft 218 to be butt-welded to the torque drive component 18.

The shaft 2 also includes space 211 between the center channel 210 and main tube 200 to accommodate and route electrical conductors 11a, 11b (shown in FIG. 2B in cross-section) for transmitting the bipolar electrosurgical energy to the end effector 3. In various exemplary embodiments, an electrically insulative material 11c, 11d may surround the electrical conductors 11a, 11b. Tendons to control wrist 4, in a manner with which those having ordinary skill in the art are familiar, also are routed through the shaft 2 in the space 211 between the center channel 210 and the main tube 200. The center channel 210 assists in isolating forces from the cables 45 acting on the torque drive component 18 and/or on the drive shaft 218, for example during roll DOF. In the depicted exemplary embodiment, the tendons include cables 45 that extend partially through and are crimped to hypotubes 245. The hypotubes 245 extend from the proximal end of the shaft 2 and terminate at a location slightly proximal to the distal end of the shaft 2. The cables 45 extend from the hypotube 245 approximately from an axial location along the spacer 215 and terminate at various the links of the wrist 4. For example, as depicted in FIG. 2A, the hypotubes 245 terminate at a location along the shaft 2 approximately at the distal end of the transition region 218b of the torque drive shaft 218. Although not shown in the various views, the tendons may include cables that extend from the proximal ends of the hypotubes to be ultimately attached to various drive components in the transmission mechanism 1. The hypotubes 245 assist in stiffening the tendons along most of the length of the shaft 2, where articulation is not occurring, and in absorbing tensile forces resulting from tensioning of the tendons when articulating the wrist 4. The cables 45 of the tendons, provided at the wrist 4 and at the transmission mechanism 1, provide a compliant, flexible structure that permits bending of the same at those locations in order to effectively apply tension. Those having ordinary skill in the art will appreciate that structures other than cables can be used for the elements 45 of the tendons, including, for example, other filament or wire structures that can withstand relatively high tensile forces to articulate the wrist 4 and relatively high flexibility to bend with the articulation of the wrist 4 and at the transmission mechanism 1.

Persons of ordinary skill in the art will understand that other shaft configurations, including placement of various channels, tendons, electrical conductors, etc. may be used to route the various elements that are used to operate the end effector 3 from input at the transmission mechanism 1 without departing from the scope of the present disclosure. However, in various exemplary embodiments, space limitations in combination with required force transmission strength and maintaining concentric operations of various components may be driving considerations when determining the routing of the various structures required to enable the various desired functions of the end effector.

Figure 15:
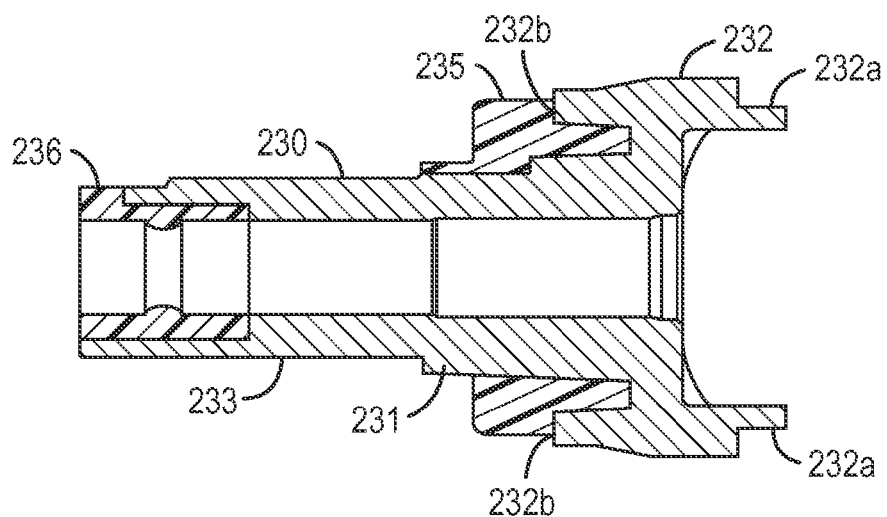
FIG. 15 is a cross-sectional view of an adapter structure and seals of FIG. 2A in accordance with an exemplary embodiment.

With reference to FIG. 2A, and the isolated detailed view of FIG. 15, to connect the distal end of the shaft 2 to the wrist 4, an adapter structure 230 is used. The adapter structure 230 has a plug-like configuration that includes a central plug portion 231 surrounded by a larger diameter head portion 232 at a distal end portion of the structure 230. A proximal end portion 233 of the central plug portion 231 has a smaller diameter and is received within the center channel 210, with the outer surface of the proximal end portion 233 and the inner surface of the center channel 210 being joined by a swaged attachment. The head portion 232 connects at its distal end 232a to a proximal link of the wrist 4 and at its proximal end 232b to the main tube 200 of the shaft 2. The outer diameter of the head portion 232 is approximately equal to the outer diameter of the wrist 4 and the shaft 2 so as to provide a substantially smooth transition between the shaft 2 and the wrist 4. In an exemplary embodiment, the adapter structure 230 can be made of stainless steel.

Figure 4:
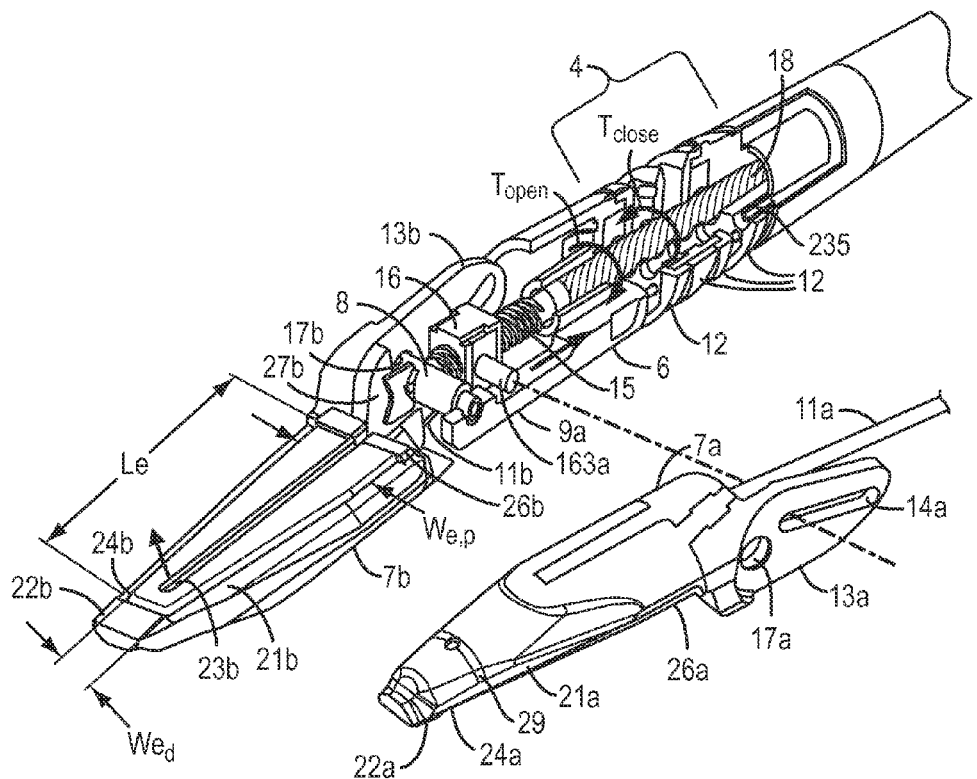
FIG. 4 is a partially exploded, partially cut-away perspective view of the end effector, wrist, and portion of the shaft of FIG. 1 in accordance with an exemplary embodiment.

In the exemplary embodiment shown in FIGS. 2A and 15, the adapter structure 230 also is provided with sealing mechanisms 235, 236 (235 also being shown in the view of FIG. 4). Sealing mechanism 235 provides liquid sealing for the tendons 45 and electrical conductors 11a, 11b at the distal end of the shaft 2. Sealing mechanism 236 provides liquid sealing for the drive shaft 218 at portion 218c. The sealing mechanisms 235, 236 can be made of various materials commonly used for seals, including, but not limited to, for example, silicone and various thermoplastic elastomers (TPEs). In particular, sealing mechanism 236 can be made of a low friction material.

Figure 3:
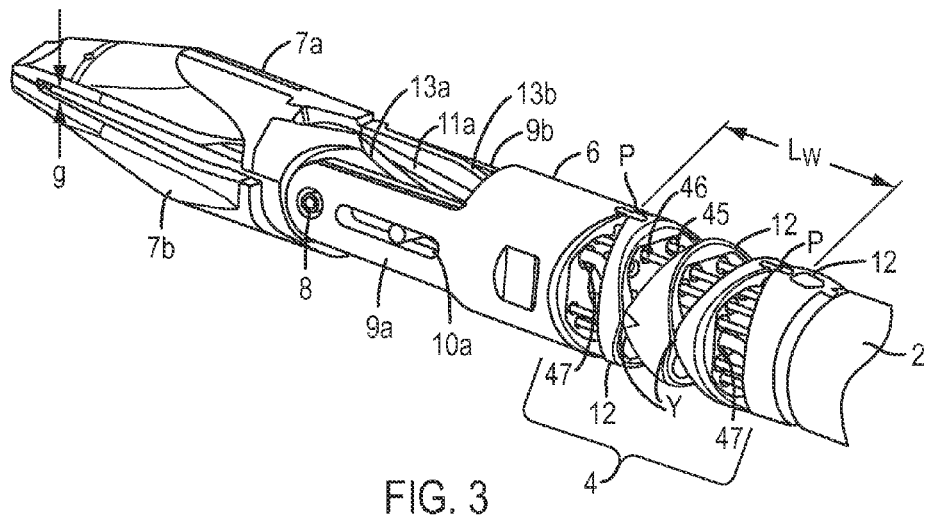
FIG. 3 is a detailed perspective view of the end effector, wrist, and portion of the shaft of the surgical instrument of FIG. 1 in accordance with an exemplary embodiment.
Figure 5:
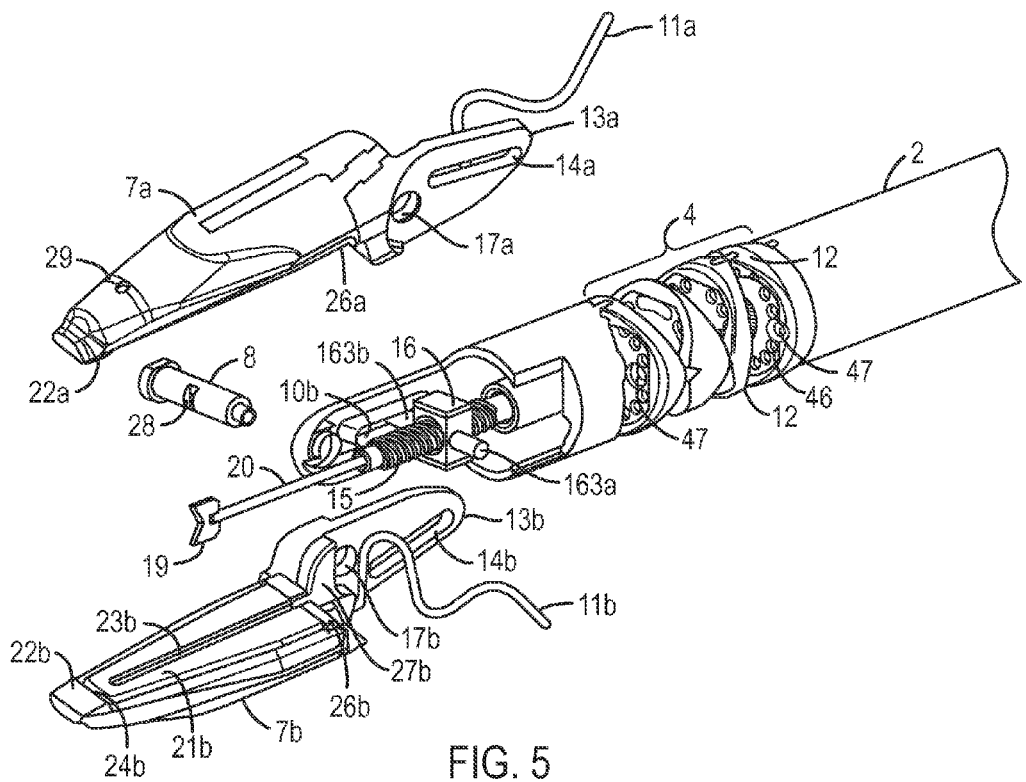
FIG. 5 is a partially exploded, partially transparent perspective view of the end effector, wrist, and portion of the shaft of FIG. 1 in accordance with an exemplary embodiment.

With reference now to FIGS. 3-5, further details of the end effector 3 and wrist 4 will now be described. FIG. 3 is a perspective view that corresponds to the detailed portion of FIG. 1, showing the end effector 3, the wrist 4, and a portion of the shaft 2. FIG. 4 shows similar portions of the instrument as FIG. 3, but is partially exploded to provide a better view of the upper jaw of the end effector 3 and partially cut away at the wrist 4 and the distal end of the shaft 2 to provide a better view of internal features of the instrument (although certain internal features have been removed for ease of illustration). FIG. 5 is a similar view as FIG. 4 with an exploded view of the jaws of the end effector and a partially transparent and cut-away view of a clevis of the end effector 3. The tendons that operate the wrist are not shown in the view of FIGS. 4 and 5.

As shown in FIGS. 3-5, the wrist 4 includes several wrist links 12. In the depicted exemplary embodiment, the links 12 are arranged in a pitch-yaw-yaw-pitch configuration (identified respectively with the labels "P" and "Y" in FIG. 3), which provides two-DOF articulation of the wrist 4. Such a configuration is nonlimiting and exemplary, however, and other combinations of links may be provided to provide a variety of pitch and/or yaw articulation along the wrist as desired. More information about the principles of wrist 4's general configuration can be found, for example, in U.S. Pat. No. 6,817,974 B2, entitled "SURGICAL TOOL HAVING POSITIVELY POSITIONABLE TENDON-ACTUATED MULTI-DISK WRIST JOINT," issued Nov. 16, 2004, which is incorporated herein by reference. Wrist actuation tendons, that include cables 45, are routed through small holes 46 disposed at an outer peripheral region of the wrist links 12 to provide wrist movement. Constant tension on the tendons, including cables 45 and hypotubes 245, keeps the links 12 together and the end effector 3 properly positioned at the distal end of shaft 2.

Figure 6:
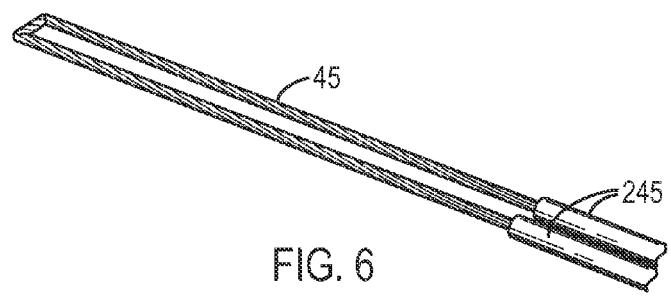
FIG. 6 is a partial perspective view of a wrist drive tendon in accordance with an exemplary embodiment.

As shown in the exemplary embodiment of FIG. 6, which shows an exemplary tendon embodiment in isolation, the cables 45 can be looped back to form a U at the distal end thereof to attach to the links 12. In the exemplary embodiment of the surgical instrument depicted, six U-shaped tendon structures as depicted in FIG. 6 can be used to control the two-DOF (e.g., pitch-yaw-yaw-pitch) articulation of the wrist 4, with three U-shaped tendons terminating (i.e., looping back) at a medial link and three U-shaped tendons terminating (i.e., looping back) at a distal link which in the exemplary embodiment includes a clevis 6 (more details of which are explained below), as shown in FIG. 2A. In various exemplary embodiments, the tendons 45 are operated under a maximum working load ranging from about 5 lbs. to about 25 lbs., for example, about 16.8 lbs., and are able to withstand a load of about 1.5 times to about 3 times the working load.

Although in the exemplary embodiments, the tendons are U-shaped and loop back at the respective links 12 of the wrist 4, it should be appreciated that the cables could be provided as single cables that terminate at their ends at the links 12 without looping back. In such a configuration, for example, the overall number of cables and hypotubes may be reduced. In some cases, in such a cable configuration it may be desirable to increase the strength of the cables from that which can be used for the U-shaped cable configuration. Those having ordinary skill in the art are familiar with various tendon configurations to operate articulating linked wrist mechanisms in minimally invasive robotic surgical instruments.

In various exemplary embodiments, the wrist 4 may have an outer diameter ranging from about 5 mm to about 12 mm, for example, from about 5 mm to about 8.5 mm, and an overall length $L_w$ ranging from about ⅜ in. to about ⅔ in. In various exemplary embodiments, the range of motion of the wrist 4 in either pitch or yaw, is +/−90 degrees and in roll is up to about +/−260°, for example, +/−180 degrees. The overall size (e.g., lateral and longitudinal dimensions) are constrained by the various motions (and corresponding drive mechanisms) that are transmitted through the wrist 4 for operation of the end effector 3, including, for example, the translation of the cutting element and the gripping of the jaws of the end effector 3. Further, the exemplary embodiments of the present teachings are able to achieve these various motions of the end effector while the wrist is articulated and rolled, for example, through the range of motion described above.

As discussed above, in an exemplary embodiment, the pitch and yaw inputs may be received by the transmission mechanism 1 via teleoperated servo actuators associated with a patient side console (e.g., patient side console 1000) of a robotic surgical system. For example, the transmission mechanism 1 may be configured like the exemplary embodiment of transmission mechanism 141 and receive pitch inputs via one input drive disk 40 and yaw inputs via another input drive disk 40, shown in FIG. 14B, and to receive an input via another drive disk 40 to rotate input shafts (one input shaft 60 being shown in FIG. 1B and the other hidden from view) within the transmission mechanism 141. Through a system of gears, links, pulleys, and a gimbal mechanism provided in the transmission mechanism, the inputs and rotation of the input shafts 60 may be transmitted, for example to increase or decrease tension in the tendons 45/245 and/or to roll the shaft 2. For various examples of transmission mechanisms that may be used to control tension in tendons to articulate jointed link wrist structures, reference is made to U.S. Pat. No. 6,817,974 B2, entitled "SURGICAL TOOL HAVING POSITIVELY POSITIONABLE TENDON-ACTUATED MULTI-DISK WRIST JOINT," issued Nov. 16, 2004, which is incorporated by reference herein in its entirety.

Figure 16:
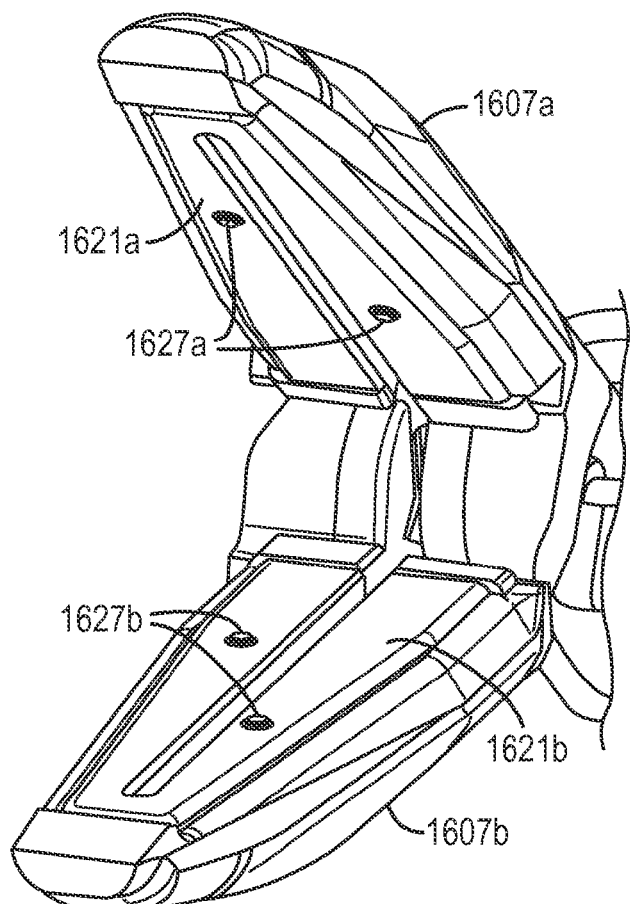
FIG. 16 is an isolated, perspective view of jaws with spacers, shown in an open position of the jaws, in accordance with an exemplary embodiment.

With reference again to FIGS. 3-5A clevis 6, mentioned above, attaches the end effector 3 to the wrist 4 and supports opposing upper and lower jaws 7a,7b of the end effector 3. Jaws 7a,7b pivot around a clevis pin 8 to move the jaws 7a, 7b between the open and closed positions. That is, jaw 7a pivots about clevis pin 8 upwardly in the orientation of the surgical instrument in the figures, and jaw 7b pivots about pin 8 downwardly. (Reference is also made to FIG. 16 showing end effector jaws 1607a, 1607b pivoted to an open position). The clevis pin 8 extends through holes in clevis ears 9a, 9b and through holes 17a, 17b provided in cam extensions 13a, 13b respectively associated with each of the jaws 7a, 7b. The clevis ears 9a, 9b each include a slot 10a, 10b (depicted in FIGS. 3 and 5). The slots 10a,10b each receive an oppositely extending protrusion 163a, 163b of a drive nut 16, as described in more detail below. Each cam extension 13a, 13b includes an angled cam slot 14a,14b disposed proximal of each hole 17a, 17b, also for receiving the respective oppositely extending protrusions 163a, 163b of the drive nut 16. As shown in the position of the instrument in FIGS. 4 and 5, the cam extension 13a provides a cam slot 14a which is angled downwardly in a direction from distal to proximal, while the cam extension 13b provides a cam slot 14b (shown in FIG. 5) that is angled upwardly in a direction from distal to proximal. As can be seen in FIG. 3, for example, the cam extensions 13a, 13b are configured to have a low profile and shape so that they are substantially flush with the outer dimensions of other portions of the surgical instrument 100, such as, for example, with the clevis 6, wrist 4, and instrument shaft 2, which can facilitate removal of the instrument, for example through a cannula.

To open and close the jaws 7a, 7b, a grip drive lead screw 15 and a grip drive nut 16 that threadingly engages with lead screw 15 can be used. FIG. 7A shows a perspective view of an exemplary embodiment of a grip drive nut 16 in isolation, and FIG. 7B shows a cross-sectional view of the grip drive nut 16 taken from the perspective 7B-7B in FIG. 7A. In the depicted embodiment, grip drive nut 16 includes a metal core 161 with an overmolded plastic casing 162. The overmolded plastic casing 162 extends within the throughhole 164 of the grip drive nut 16 and is formed with threading that engages with the threading on the lead screw 15 to reduce friction. The overmolded plastic casing 162 provides overall structural strength to the grip drive nut 16, including to the threading. Also, the overmolded plastic threading assists in increasing nut position precision as lead screw 15 turns. Further, the plastic casing 162 is disposed on the top, bottom, front, and back faces of the nut 16 (in the orientations of FIGS. 3-5 and 7), and extends along the edges of the side faces of the nut 16 surrounding the metal core. The plastic casing 162 helps to reduce friction, and thereby promote position precision, as the nut's 16 surfaces contact the clevis 6 and the cam extensions 13a, 13b during its movement along the lead screw 15. Drive nut 16 also includes two engagement pins 163a, 163b at opposite sides of the nut 16. Each pin 163a, 163b extends through an associated cam slot 14a,14b and associated slot 10a, 10b in the clevis 6.

In an exemplary embodiment, the threading in the throughhole 164 of the grip drive nut 16 is a multi-start threading, and has a lead of about 0.1 in. per rotation. Providing a multi-start threading can facilitate manufacturability of the nut and the lead screw, improve strength, and/or facilitate movement of the nut in two directions along the lead screw. Also, in an exemplary embodiment, the core 161 of the nut 16 can comprise stainless steel, for example, a stainless steel alloy, such as, for example, 17-4 stainless steel. The overmolded plastic portion 162 can comprise a relatively high strength, low friction plastic capable of being applied to adhere to the metal core.

The lead screw 15 is located distally against clevis pin 8 to maintain its position relative to the shaft 2 and connects at its proximal end to the torque drive component 18. The connection to the torque drive component 18 may, for example, be accomplished via a butt-weld of the proximal end of the lead screw 15 to the distal end of the torque drive component 18, but such connection is non-limiting and exemplary only. Although not shown in the figures, a distal, nonthreaded end of the lead screw 15 can be received in a counterbore hole provided in clevis pin 8 disposed substantially opposite to a notch 28 in the clevis pin 8 that receives the cutting blade 19 of the cutting element. Accordingly, as shown in FIGS. 4 and 5, the lead screw 15 is positioned distal to the wrist 4, substantially within the clevis 6. The clevis pin 8 acts as a distal stop that prevents movement of the lead screw 15 in the distal direction beyond the clevis pin 8. In an exemplary embodiment, a proximal stop, such as for example, a thrust ball bearing (not shown) provided in the transmission mechanism 1 can prevent the lead screw 15 from moving too far in a proximal direction. In an exemplary embodiment, the thrust ball bearing may be disposed in the chassis of the motor assembly including the rack and pinion 50 shown in the exemplary embodiment of FIG. 14A, with the hollow drive shaft 218 positioned proximate the chassis so as to absorb an axial thrust load of the hollow drive shaft 218 and lead-screw assembly as the assembly moves in the proximal direction when the jaws 7a, 7b are opened. Reference is made to U.S. Provisional Patent Application No. U.S. 61/491,698, entitled "SURGICAL INSTRUMENT WITH MOTOR" (filed May 31, 2011) and to U.S. Provisional Patent Application No. U.S. 61/491,671, entitled "SURGICAL INSTRUMENT WITH CONTROL FOR DETECTED FAULT CONDITION," (filed May 31, 2011), both of which are incorporated by reference herein in their entireties.

Thus, as the lead screw 15 rotates (via the rotational movement of hollow drive shaft 218 and torque drive component 18, as described further below), drive nut 16 travels along lead screw 15. Movement of the drive nut 16 along the lead screw 15 in turn moves the pins 163a, 163b along the associated cam slots 14a, 14b to open and close the jaws 7a, 7b. That is, as drive nut 16 travels in the distal direction, jaws 7a, 7b pivot about the clevis pin 8 to move the jaws 7a, 7b to the open position. As the drive nut 16 travels in the proximal direction, jaws 7a, 7b pivot about the clevis pin 8 to move the jaws 7a, 7b to the closed position. The location of the pins 163a, 163b at the distal end of the cam slots 14a, 14b defines the fully open position of the jaws 7a, 7b. The location of the pins 163a, 163b proximally in the cam slots 14*a*, 14*b* (i.e., approximately in the position shown in FIG. 3, somewhat distal to the proximal ends of the cam slots 14*a*, 14*b*) defines the fully closed position of the jaws 7*a*, 7*b*. Defining the fully closed position of the jaws 7*a*, 7*b* to correspond to a position of the pins 163*a*, 163*b* somewhat distal to the proximal ends of the cam slots 14*a*, 14*b* helps to ensure that the pins 163*a*, 163*b* bearing against the cam slot surface does not stop achieving full closure of the jaws 7*a*, 7*b*. As mentioned above, in various exemplary embodiments, the lead screw 15 may ultimately be coupled, e.g., through its drive mechanism, to a torque-limiting spring that acts as the mechanism by which the fully closed position of the jaws 7*a*, 7*b* is defined, as described, for example, in U.S. Provisional Patent Application No. U.S. 61/491,804 (filed May 31, 2011)," incorporated by reference in its entirety herein.

The lead screw and nut combined with the pivoting cam slots 14*a*, 14*b* enables a strong grip force to be achieved by the jaws 7*a*, 7*b*, even within compact space restraints and various, relatively large range of DOF movements of the instrument. In various exemplary embodiments, the cam slots 14*a*, 14*b* can provide a clamped mechanical advantage of about 4:1 in converting the linear motion of the nut 16 to the gripping motion of the jaws 7*a*, 7*b*. Persons of ordinary skill in the art will understand that various other jaw activation mechanisms are available, and in other embodiments only a single moving jaw may be used, with the other, opposing jaw being fixed in position. Positioning each of the pins 163*a*,163*b* through its associated clevis ear slot 10*a*,10*b* helps prevent the drive nut 16 from twisting within the clevis 6 to provide enhanced stability of the motion of the nut and thus opening and closing of the jaws 7*a*,7*b*.

To transmit the torque necessary to turn lead screw 15 through wrist 4, including through a relatively large range of articulation (e.g., orthogonal pitch and/or yaw articulation) of wrist 4 and/or roll of the instrument, a torque drive component 18 that connects to and is driven by drive shaft 218 is used in accordance with various exemplary embodiments. In various exemplary embodiments, a torque drive component 18 that may be used includes a multi-layered, tubular cable structure. The layered structure may have adjacent layers that comprise windings of differing directions, as explained in further detail with reference to the exemplary embodiment depicted in FIGS. 8A and 8B. Although the exemplary embodiment of FIGS. 8A and 8B include three layers of windings, the present disclosure is not limited to three layers. Rather, torque drive components in accordance with various exemplary embodiments can include two or more layers of windings, for example, with each layer having helical turns in differing directions.

FIGS. 8A and 8B show one exemplary embodiment of a torque drive component 18 that includes a tubular structure of three layers of relatively tightly wound windings (coils) 181, 182, 183 (shown best in the cross-sectional view of FIG. 8B). An inner winding 181 and an outer winding 183 each twists so as to provide helical turns traversing along the tube in a first direction. A middle winding 182 is disposed between the inner and outer windings and twists so as to provide helical turns traversing along the tube in a second direction opposite to the first direction. The first direction of twist is oriented to provide compression of the inner winding 181 and the outer windings 183 against themselves in the direction that moves the lead screw 15 so as to move the jaws 7*a*, 7*b* to the closed position. Accordingly, as can be seen in FIGS. 4 and 5, the helical pattern of the threading on the lead screw 15 and the outer winding 183 are in the opposite direction. In particular, in the exemplary embodiment depicted, the outer winding 183 has a helical pattern of windings that rise from right to left in the clockwise direction and the threading on the lead screw 15 rises from left to right in the clockwise direction. The torque $T_{close}$ (shown in FIG. 4) required to move the jaws 7*a*, 7*b* to the closed position to provide a sufficient gripping force is higher than the torque $T_{open}$ (also shown in FIG. 4) required to move the jaws 7*a*, 7*b* to the open position. Accordingly, the two inner and outer windings 181, 183 are provided to withstand this higher torque. Since torque drive component 18 is a hollowed cable structure, it flexes substantially equally in all directions, including pitch and yaw, and combinations thereof, with low friction. Thus, the torque drive component 18 provides a relatively low bending force with a relatively high torque transmission capability to achieve transmission of a torque through wrist 4 sufficient to turn lead screw 15 without significantly limiting wrist 4's articulation and roll DOFs. With regard to the latter, flexibility in all directions facilitates maintaining concentricity of the various elements during roll DOF.

In one instance, the gripping pressure of the jaws 7*a*, 7*b* in the closed position was sufficient to achieve vessel sealing with the wrist articulated in the range of at least about 60 degrees in various directions (i.e., pitch and/or yaw). In various exemplary embodiments, the tip force exerted by the jaws 7*a*, 7*b* when in the closed position ranges from about 4.25 lbs to about 8.75 lbs, throughout a range of wrist articulation of at least about +/−60 degrees in various directions (i.e., pitch, yaw, or combinations thereof). Further, in various exemplary embodiments, the jaws 7*a*, 7*b* are configured in the closed position to provide a sufficiently high gripping pressure in order to effect sealing (fusing) of the tissue (e.g., vessel). By way of nonlimiting example, the pressure exerted by the jaws 7*a*, 7*b* on the tissue in the closed position ranges from about 80 psi to about 220 psi, for example from about 95 psi to about 200 psi.

In various exemplary embodiments, the inner winding 181 may have an outer diameter of about 0.045 in. and a pitch of about 0.125 Left Hand Lay; the middle winding 182 may have an outer diameter of about 0.059 in. and a pitch of about 0.110 Right Hand Lay; and the outer winding 183 may have an outer diameter of about 0.0775 in. and a pitch of about 0.140 Left Hand Lay.

In another exemplary embodiment, for example, as described in more detail below with reference to the embodiment of FIG. 17, a portion of the outer surface of the outer layer of the multi-layered torque drive component can be removed, for example, via grinding, to provide a smoother surface, which in turn can result in increased flexibility of the torque drive component, greater consistency of the grip force, and/or increase the clearance between the torque drive component and the wrist.

In an exemplary embodiment, a spring, for example, provided in the transmission mechanism 1, may be used to assist in closing the jaws 7*a*, 7*b*, particularly to help close the jaws 7*a*, 7*b* when it is desirable to back the surgical instrument 100 through a cannula away from the surgical site. Such a spring-actuated mechanism can help to prevent damage to the end effector 3 if the jaws 7*a*, 7*b* are not placed in the closed position prior to retracting the instrument through a cannula. For additional details on providing a spring-actuation mechanism to assist in closing the jaws of a cutting/fusing minimally invasive, robotically controlled surgical instrument, reference is made to U.S. Provisional Patent Application No. U.S. 61/491,798 and U.S. patent application Ser. No. 13/297,168, both entitled "DECOUPLING INSTRUMENT SHAFT ROLL AND END EFFEC- TOR ACTUATION IN A SURGICAL INSTRUMENT" (filed May 31, 2011 and Nov. 15, 2011, respectively), both of which are incorporated by reference herein in their entirety.

Those having ordinary skill in the art will appreciate that the direction of the various windings/threading, along with the direction of the input torques ($T_{open}$ and $T_{close}$), shown in the illustrations of FIGS. 4, 5, 8A, and 8B can be reversed without departing from the scope of the present teachings.

Figure 9:
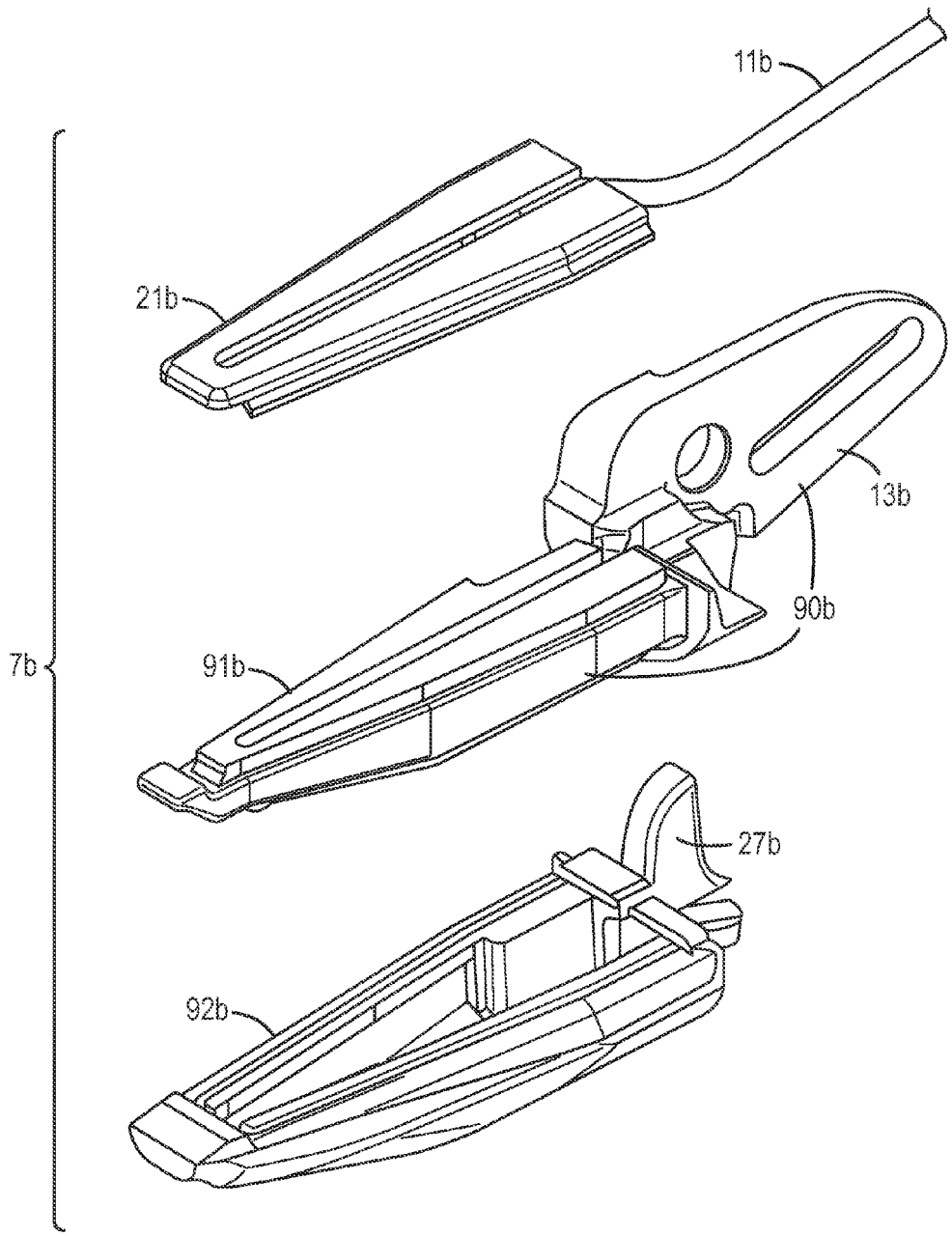
FIG. 9 is an exploded view of a jaw assembly in accordance with an exemplary embodiment.

With reference now to FIG. 9, in an exemplary embodiment, each jaw 7a,7b (FIG. 9 depicts only one jaw 7b; the other jaw 7a is similarly constructed) can include a metal core part 90b which includes the cam extension 13b, an electrode support part 91b, and an outer cover part 92b. The electrode support part 91b and outer cover part 92b can comprise a plastic material. The electrode support part 91b insulates the electrode 21b from the metal core. The outer cover part 92b receives and supports the combined metal core part 90b and electrode support part 91b. The metal core part 90b can provide strength to the jaws 7a, 7b to enable the jaws 7a, 7b to withstand the forces associated with gripping, for example, with minimal deflection. In various exemplary embodiments, the metal core part 90b can comprise stainless steel or a stainless steel alloy, such as, for example, 17-4 stainless steel. The electrode support part 91b and the outer cover part 92b can be made by overmolding plastic around the metal core part 90b, such as, for example, a glass-filled polyphthalamide (PPA), for example, a 10- to 30-percent glass filled PPA.

In various exemplary embodiments, the jaws 7a, 7b can be formed using a multi-shot molding process. The electrode support part 91b can be formed in a first shot of a mold and the outer cover part 92b in a second shot of the mold. In an exemplary embodiment, the metal core part 90b can be obtained by metal injection molding (MIM). In an alternative embodiment, the metal core part 90b can be machined. The electrode 21b can be positioned over the electrode support part 91b, and secured thereto during the second shot molding step. Persons of ordinary skill in the art will appreciate that jaw 7a can be formed in the same manner as jaw 7b.

As described herein, in addition to gripping, the jaws 7a, 7b of the end effector 3 are configured to deliver electrosurgical energy to fuse tissue together, for example, to fuse tissue of a dissected vessel in order to seal the ends of the dissected vessel. Referring again to FIGS. 4 and 5, each jaw 7a,7b includes an electrode 21a, 21b that receives energy from the associated electrical conductors 11a, 11b. In various exemplary embodiments, each electrode 21a, 21b receives one pole from a bipolar energy source to create bipolar energy between the electrodes sufficient to fuse tissue. In various exemplary embodiments, the voltage of the energy source may be about 220 $V_p$ at a frequency ranging from about 100 Hz to about 400 Hz, and the power may be about 240 W to about 360 W, and the temperature of the electrodes 21a, 21b can be about 100° C. In various exemplary embodiments, the electrodes 21a, 21b may be stainless steel and control algorithms for conducting the electrical energy through the electrical conductors 11a, 11b can be implemented via a teleoperated robotic surgical system, for example, using the central control console 3000, as depicted in the exemplary embodiment of FIGS. 12A and 12B. In various exemplary embodiments, bipolar energy source algorithms, such as, for example, those available in electrosurgical generator products from ErbeElektromedizin, GmbH, Germany, can be implemented (e.g., via generator 3090 in FIG. 12B) to prevent tissue sticking to the electrodes 21a, 21b. The electrical conductors 11a, 11b can be any suitable conductive wire protected with an insulation layer surrounding the wire. In one exemplary embodiment, the electrical conductors 11a, 11b can include a copper alloy wire with an ethylene tetrafluoroethylene (ETFE) insulation layer.

The length, $L_e$, of each of the electrodes 21a, 21b in various exemplary embodiments may range, for example, from about 16 mm to about 18 mm, which may be desirable for sealing a vessel having a diameter of about 7 mm. The width of the electrodes 21a, 21b, as well as the corresponding jaws 7a, 7b, can present a generally tapered shape, having a larger width at the proximal end and a narrower width at the distal end. Such a tapered shape can be beneficial for dissection of tissue, including dissection of vessels. For example, the tapered shape can improve visibility during dissection and can provide a smaller contact area to pierce tissue. In various exemplary embodiments, the width at the proximal end, $W_{e,p}$, ranges from about 2.5 mm to about 5.5 mm, for example, the width may be about 5 mm; and the width, $W_{e,d}$, at the distal end ranges from about 2.5 mm to about 3.5 mm, for example the width may be about 3 mm. The width of the electrodes 21a, 21b can be selected to provide fusing of both sides of dissected tissue (e.g., dissected ends of a vessel) gripped between the jaws 7a, 7b. For example, the width may be selected to provide at least about a 1 mm seal on either side of the dissected tissue. The thickness of each electrode 21a, 21b in various exemplary embodiments may range from about 0.005 in. to about 0.015 in., for example, the thickness may be about 0.010 in. To assist in preventing tissue from sticking to the electrodes 21a, 21b, the surfaces of the electrodes can be finished with a micro-inch surface finish, for example, an 8 micro-inch surface finish.

As shown, each of the electrodes 21a, 21b is provided with a groove 23b (corresponding groove on electrode 21a is hidden from view in FIGS. 3-5) configured to receive and provide a track for the cutting element as it translates in the proximal and distal directions relative to the jaws 7a, 7b, as will be described in further detail below. In a closed position of the jaws 7a, 7b, the electrodes 21a, 21b are maintained spaced apart from each other to provide a gap g (see FIG. 3) by spacer lips 22a, 22b disposed at the distal end of each jaw 7a, 7b, and by spacer bars 26a, 26b at a proximal end of the electrodes 21a, 21b. The height of the spacer bars 26a, 26b above the surface of the electrodes 21a, 21b may be slightly lower than the height of the spacer lips 22a, 22b above the electrode surfaces to promote a uniform gap g across the length of the electrode surfaces while also permitting the electrode surfaces come sufficiently close along their entire length to ensure effective gripping and sealing of tissue.

Those having ordinary skill in the art will appreciate that other configurations of spacing structures may be utilized in addition to or in lieu of either the spacer lips 22a, 22b and/or spacer bars 26a, 26b. For example, spacer structures can be placed in locations along the length of the electrode surfaces to maintain a gap between the electrode surfaces when the jaws 7a, 7b are in a closed position. By way of example only, in one embodiment as depicted in FIG. 16, jaws 1607a, 1607b can include spacer structures 1627a, 1627b on the upper surfaces of the electrodes 1621a, 1621b, located, for example, in a central portion along a length of the electrodes 1621a, 1621b. In an exemplary embodiment, the spacer structures 1627a, 1627b can be formed by providing throughholes in one or both electrodes 1621a, 1621b, and then mold material underlying the respective electrodes 1621a, 1621b can be permitted to flow through the throughholes and beyond the electrode surfaces. The mold material that rises above the electrode surfaces can form the spacer structures 1627a, 1627b. In this way, the spacer structures and the underlying electrode support part (e.g., like electrode support part 92b in FIG. 9) are combined as a single piece. Providing spacer structures in this manner may permit relatively small spacers to be placed along the length of the electrode using a relatively simple fabrication process. Of course those having ordinary skill in the art will appreciate that the forming of such spacer structures is not limited to the fabrication process described above and a variety of techniques for providing such spacer structures along the electrode surfaces can be used. Further, although the exemplary embodiment of FIG. 16 illustrates two spacer structures on both electrodes 1621a, 1621b, any number of such spacer structures can be provided on one or both electrodes 1621a, 1621b, as desired.

In various exemplary embodiments, the gap g (shown in FIG. 3) between the electrodes 21a, 21b when the jaws 7a, 7b are in the closed position is on the order of a few thousandths of an inch, for example, about 0.004 inches.

As shown in FIGS. 4 and 5, in each jaw 7a, 7b, a small recess 24a, 24b extending substantially across the width of each jaw 7a, 7b can be placed distally of the associated electrode 21a, 21b, i.e., between the electrodes 21a, 21b and the spacer lips 22a, 22b. The recesses 24a, 24b can accommodate tissue gripped between the jaws 7a, 7b to assist in preventing gripped tissue from sliding out of the grip of the jaws 7a, 7b through the distal end of the end effector 3. The spacer lips 22a, 22b also can assist in preventing tissue from sliding through the distal end of the end effector 3. In one exemplary embodiment, the recesses 24a, 24b can have a depth ranging from about 0.1 mm to about 0.4 mm.

Also, in various exemplary embodiments, the upper jaw 7a can include a marking, e.g., in the form of a line 29 extending transverse the upper jaw 7a. The placement of the line 29 is selected so as to provide an observable indicator to a surgeon of the extent to which the cutting mechanism will travel along the jaws 7a, 7b during a cut operation. In this way, the surgeon can have a visible indicator that tissue captured in the jaws 7a, 7b that lies between the line 29 and the garage position of the cutting blade (described in further detail below) will be in the path of the cutting blade during a cutting procedure. In an exemplary embodiment, the marking 29 can be made by laser-marking the jaw.

To avoid interfering with surgery or passage through a cannula, the electrical conductors 11a,11b are recessed in the end effector 3 and are routed proximally back through the side channels 47 (shown in FIGS. 3 and 5) in the wrist 4 and then through the shaft 2, as described above with reference to FIGS. 2A and 2B. The electrical conductors 11a, 11b ultimately connect to a power generator source that may, for example, be located at the central control console 3000 of a teleoperated robotic surgical system depicted in FIGS. 12A and 12B. In an exemplary embodiment, a separate one or more separate controllers 3080/3090 added to a central control console 3000 may have a power connection to supply power to the electrical conductors 11a, 11b; alternatively, the power source may be integrated with the central control console 3000. Further, in various exemplary embodiments, to minimize interference with operation of the end effector 3, particularly opening and closing the jaws 7a, 7b, the electrical conductors 11a, 11b can be provided with slack when they are positioned against the jaws 7a, 7b, as illustrated in the exemplary embodiment of FIG. 5.

As described above, in addition to gripping and fusing, the surgical instrument 100 can be configured to cut. As illustrated in FIG. 5, the end effector 3 thus also includes a cutting element in the form of a short cutting blade 19 (shown also in FIGS. 10 and 11). Cutting blade 19 is translated distally and proximally relative to end effector 3 by a cutting element drive component 20. The cutting blade 19 travels between a proximal-most, so-called "garaged" position and a distal-most position. In the proximal-most, "garaged" position, the proximal end of the cutting blade 19 is received in a notch 28 provided in the clevis pin 8 and is protected on its sides by opposing garage features (only 27b being shown in FIGS. 4, 5, 9, and 11, and similar features being hidden from view for jaw 7a) that are adjacent to the opposing surfaces of the cam extensions 13a, 13b. The opposing garage features 27b help to protect tissue from entering into the proximal end of the jaws 7a, 7b and potentially contacting the cutting blade 19. In the distal-most position, the distal end of the cutting blade 19 is positioned at a distal end of the grooves 23a, 23b respectively provided on the opposing electrode surfaces 21a, 21 b of the jaws 7a, 7b. Since the cutting element drive component 20 is generally flexible, as will be described, the grooves 23a, 23b keep the cutting blade 19 aligned as it travels along the jaws 7a, 7b.

Figure 11:
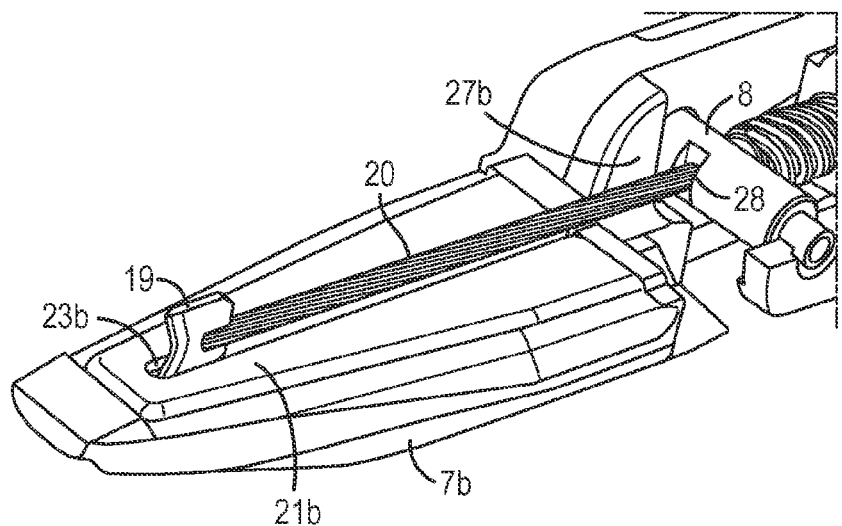
FIG. 11 is a partial isolated, perspective view of the bottom jaw and cutting element of the end effector of FIGS. 3-5 in accordance with an exemplary embodiment.

With reference to FIG. 11, the position of the cutting blade 19 relative to the bottom jaw 7b when the cutting blade 19 is in the distal-most position is shown. Accordingly, throughout its translation, the cutting blade 19 stays within the end effector 3; additionally, in its garaged position shown in FIG. 4, the cutting blade 19 is retracted behind the electrode surfaces 21a, 21b substantially within the clevis pin 8 and garage features (27b described above and corresponding element associated with jaw 7a) of the end effector 3. Moreover, to enhance safety of operation of the surgical instrument 100, operation (i.e., translation) of the cutting element 19 from the garaged position can be prevented from occurring unless the jaws 7a, 7b are in the closed position. In an exemplary embodiment, this can occur via a controller and software that controls the operation to drive the cutting element drive component 20, as taught for example in U.S. Provisional Patent Application No. U.S. 61/491,647, entitled "POSITIVE CONTROL OF ROBOTIC SURGICAL INSTRUMENT END EFFECTOR," (filed May 31, 2011), incorporated by reference in its entirety herein. For other control features that may be implemented for a cutting element that is controlled and driven using a robotic surgical system (e.g., which can include use of an onboard motor like motor 5 in FIG. 14A), reference is made to U.S. Provisional Patent Application No. U.S. 61/491,698, entitled "SURGICAL INSTRUMENT WITH MOTOR" (filed May 31, 2011) and to U.S. Provisional Patent Application No. 61/491,671, entitled "SURGICAL INSTRUMENT WITH CONTROL FOR DETECTED FAULT CONDITION" (filed May 31, 2011), both incorporated by reference herein. In one exemplary embodiment, a software feature prevents actuation of the cutting blade 19, for example via control of motor 5, until the jaws 7a,7b are sufficiently closed to allow cutting blade 19 to extend safely within slots 23a, 23b, without risk of the cutting element coming out of the slots 23a, 23b and potentially outside of the jaws 7a, 7b.

Figure 10:
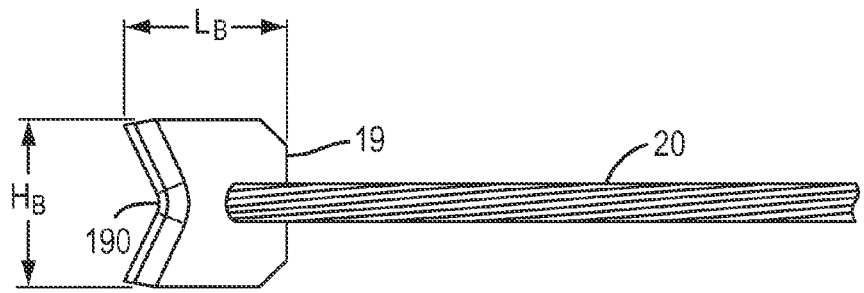
FIG. 10 is an isolated, partial side view of a cutting element and cutting drive component in accordance with exemplary embodiments.

In the exemplary embodiments illustrated in FIGS. 5 and 10, as discussed above, the cutting element drive component 20 is a cable having a distal end that is welded to the proximal end of the cutting blade 19. To avoid sharp edges and/or blunt surfaces where the blade 19 attaches to the cable 20, the blade 19 and cable 20 may be blend welded together to provide a smooth interface between the two components. Providing a relatively smooth interface between the two components can reduce the risk of having the cutting element become stuck on tissue during a cutting procedure. The drive component 20 is attached at a proximal end to the transmission mechanism 1, which is configured to provide a linear (push/pull) motive force to the drive component 20 and allow roll DOF, and as described above, is routed centrally through the shaft 2 and wrist 4 to the end effector 3. The cable structure of the drive component 20 is sufficiently flexible so as to withstand bending in various directions about its longitudinal axis, while also providing sufficient compressive and tensile strength to withstand and transmit the push/pull actuation forces from the transmission mechanism 1 to translate the cutting blade 19, including through tissue in order to effect cutting. The central routing of the drive component 20 through the shaft and wrist 4 permits the surgical instrument 100 to have a relatively compact design while also providing centering of the cutting blade 19 relative to the end effector 3 during the cutting operation. Further, central routing of the drive component 20 can reduce friction that acts on the drive component 20 as it moves through wrist 4, particularly when wrist 4 is articulated and/or rolled, when translating the cutting blade 19. In this way, the force required to drive the cutting blade 19 can be reduced in comparison with a configuration in which the drive component 20 is routed toward an outer periphery of the instrument 100 as opposed to centrally. Further, central routing of the cutting drive component 20 can result in substantially no change of length during articulation of the wrist 4, allowing the cutting blade 19 to remain in the garaged position during articulation.

In an alternative embodiment (not shown), rather than a cable structure, the drive component 20 can include a superelastic flexible wire having a high tensile and compressive strength, such as, for example, a nitinol wire. In at least one exemplary embodiment, the cutting blade 19 also can be made of nitinol.

The lead screw 15 and torque drive component 18 are both hollow, and cutting element drive component 20 is routed through the hollow centers of the lead screw 15 and the torque drive component 18. Thus, the resulting combined structure of the torque drive component 18 and the cutting element drive component 20 flexes equally in pitch, yaw, and combinations of pitch and yaw, with relatively low friction as the combined structure passes through wrist 4. In this way the grip DOF and cutting element translation DOF can be transmitted through wrist 4 to end effector 3 in a compact configuration that allows the relatively small wrist 4 to operate in Cartesian pitch, yaw, and roll DOFs. As a result, a minimally invasive surgical instrument is provided that has an end effector with integrated tissue fusing and cutting functions and a wrist mechanism that allows the end effector to be oriented in Cartesian pitch, yaw, and roll (roll is enabled by changing wrist 4 pitch and yaw as necessary as shaft 2 rolls).

With reference to FIG. 10, in one exemplary embodiment, the cutting blade 19 has a concave "V" shape cutting surface 190, which can assist in pulling tissue into the cutting surface. However, such configuration is non-limiting and exemplary only, and in other configurations the blade may have a straight, angled, or curved cutting surface. As shown in FIG. 10, in an exemplary embodiment, the proximal end of the cutting blade 19 may have rounded top corners to minimize the risk of the cutting blade 19 getting stuck when back-driven after completion of a cutting procedure. In various exemplary embodiments, the blade 19 is made of stainless steel (e.g., 716 stainless steel) and has a double grind cutting surface. The blade 19 can be secured to the drive component 20 by various mechanisms, including, for example, welding. In various exemplary embodiments, the blade 19 has a height, $H_B$, ranging from about 0.08 in. to about 0.15 in., for example about 0.10 in., and a length, $L_B$, ranging from about 0.10 in. to about 0.13 in., for example, about 0.115 in.

As mentioned above, in one exemplary embodiment, the cutting mechanism drive component 20 can be actuated via an onboard motor disposed in the transmission mechanism 1, for example, via an onboard motor 5 in conjunction with a worm gear and rack and pinion mechanism 50 as illustrated in the exemplary embodiment of transmission mechanism 141 shown in FIG. 14A. To control the movement of the cutting blade 19, one or more limit switches 55 (one being shown in the exemplary embodiment of FIG. 14A) can be used to sense the position of the cutting blade 19. For one exemplary embodiment of using a limit switch to sense the position and assist in controlling the operation of the cutting blade, reference is made to U.S. Provisional Patent Application No. U.S. 61/491,698, entitled "SURGICAL INSTRUMENT WITH MOTOR" (filed May 31, 2011) and to U.S. Provisional Patent Application No. U.S. 61/491,671, entitled "SURGICAL INSTRUMENT WITH CONTROL FOR DETECTED FAULT CONDITION" (filed May 31, 2011), both incorporated by reference herein. Of course, those having ordinary skill in the art will appreciate that a variety of actuation mechanisms, including but not limited to, for example, servo actuators associated with a teleoperated robotic surgical system or a manually driven actuator can be utilized to control the movement of the drive component 20. Further, in exemplary embodiments that rely on robotic control to actuate the cutting element drive component 20, the instrument 100 can be provided with a feature that permits the cutting element 19 to be manually retracted, such as, for example, via a hex wrench or other tool configured to engage through the chassis of the transmission mechanism, for example, with a worm gear used to drive the cutting element drive component.

As mentioned above, in various exemplary embodiments, the outer diameter of shaft 2, end effector 3 (in a closed position), and wrist 4 ranges from about 5 mm to about 12 mm, for example from about 5 mm to about 8.5 mm, for example, the outer diameter may be about 8.5 mm in one exemplary embodiment. Consequently, tissue fusing and cutting surgical instruments in accordance with various exemplary embodiments can be inserted through a patient's body wall by using a cannula capable of inserting other 5 mm or 8.5 mm class telerobotic surgical instruments. In the case of such 5 mm or 8.5 mm outer diameter cutting and fusing surgical instrument, the outer diameter is about thirty-eight percent smaller than the outer diameter of a 13 mm wristed stapling surgical instrument. Moreover, in the case of performing cutting and fusing surgical procedures, smaller diameters have advantages for visualization and access in such procedures that may be more delicate and/or difficult to perform, and generally within smaller spaces.

In various exemplary embodiments, the surgical instrument 100 may be configured as a single-use, disposable surgical instrument. Accordingly, to reduce costs associated with manufacturing the surgical instrument yet provide an instrument sufficiently strong to perform the various operations required, various components are made of plastic and are formed using an injection molding process. In addition, where additional strength for a component is desirable, various components or parts thereof may be made using a metal injection molding (MIM) process. By way of non-limiting example, in the transmission mechanism 1, various gears, gimbal plates, pulleys, links, etc. may be made of plastic, machined metal, stamped sheet metal, powdered metal, and/or MIM parts. Moreover, in the case wherein an onboard motor is used as an actuator, for example, to drive the cutting element, such a motor can be a relatively inexpensive motor, such as, for example, a DC motor configured to deliver sufficient force when operating with voltage inputs ranging from about 5 V to about 15 V, for example, about 5.5 V to about 10 V.

An exemplary method for using the surgical instrument 100 for performing tissue fusing and cutting will now be described with reference to exemplary steps illustrated in the flow diagram of FIG. 13. In an exemplary embodiment, as shown at 1301 in FIG. 13, the surgical instrument 100 can be inserted (e.g., laparoscopically or thoracoscopically) into the body of a patient, for example, through a cannula, and advanced to a position generally in the proximity of a work site at which a cutting and fusing procedure is desired. After insertion and advancement of the surgical instrument 100 to the desired work site, as shown at 1302, the transmission mechanism 1, 141 can receive one or more inputs (e.g., at input disks 40 in the exemplary embodiment of transmission mechanism 141) to roll and/or articulate the wrist 4, such as, for example, via roll, pitch, yaw, or a combination of any of those motions. As explained above, the transmission mechanism 1 can transmit the inputs into various forces and/or torques to ultimately actuate (drive) the overall instrument shaft 2 (for example via roll) and/or to modify the tension in tendons 45 to articulate the wrist 4 in pitch and/or yaw.

Once the end effector 3 is in a desired position and orientation, at 1303 in FIG. 13, the transmission mechanism 1 (e.g., at input disks 40 in the exemplary embodiment of transmission mechanism 141) can receive an input to open the jaws 7a, 7b of the end effector 3 and the instrument 100 can be advanced such that tissue for which fusing/cutting is desired is positioned between the opened jaws 7a, 7b. As explained above, the transmission mechanism 1 can transmit the input to open the jaws 7a, 7b by exerting a torque in a first direction on the hollow drive shaft 218 and torque drive component 18, which torque can be transmitted to rotate lead screw 15 and to move the drive nut 16 along the lead screw 15 toward a distal end of the end effector 3. With the tissue positioned as desired between the open jaws 7a, 7b, the transmission mechanism 1 (e.g., at input disks 40 in the exemplary embodiment of transmission mechanism 141) can receive, as shown at 1304 in FIG. 13, an input to close the jaws 7a, 7b in order to grip the tissue. As explained above, the transmission mechanism 1 can transmit the input to close the jaws 7a, 7b by exerting a torque in a second direction, opposite to the first direction, on the hollow drive shaft 218 and torque drive component 18, which torque can be transmitted to rotate lead screw 15 and to move the drive nut 16 along the lead screw 15 toward a proximal end of the end effector 3.

Next, as shown at 1305 in FIG. 13, with the jaw 7a, 7b in a closed position gripping the tissue, electrosurgical energy (e.g., bipolar energy) can be passed through the electrical conductors 11a, 11b to activate the electrodes 21a, 21b. The bipolar energy transmitted to the electrodes 21a, 21b is sufficient for the electrodes 21a, 21b to fuse the tissue gripped between them. In an exemplary embodiment, at 1306, a signal, such as for example, an audible signal (e.g., a beep or otherwise) and/or a visible signal observable for example on a monitor or other display, can be provided to the instrument operator to confirm that the tissue fusing has been completed.

Upon completion of fusing, at 1307 in FIG. 13, an input can be provided to the transmission mechanism 1 to drive the cutting element. As explained above, upon receiving the input, the transmission mechanism 1 can transmit various forces and torques to ultimately drive the cutting element drive component 20, for example, using push/pull forces on the same. In an exemplary embodiment, the cutting element drive component 20 can be actuated to drive the cutting element from the garaged position, to the distal most position, and back to the garaged position using a single input to the transmission mechanism 1. Accordingly, the entire cutting translation motion (i.e., from the garaged position to the distal most position and back) can be automatically completed. In an exemplary embodiment, particularly in use with a robotic surgical system such as that depicted in FIGS. 12A and 12B, the cutting operation may be prevented from occurring, e.g., through the use of appropriate algorithms and feedback sensors controlled by a controller such as integrated with or located as a separate unit of a central control console 3000, if the jaws 7a, 7b are not in the closed position. Reference is made to U.S. Provisional Patent Application No. U.S. 61/491,647, entitled "POSITIVE CONTROL OF ROBOTIC SURGICAL INSTRUMENT END EFFECTOR," (filed May 31, 2011), incorporated by reference in its entirety herein.

Once the cutting procedure has been completed, the instrument 100 can be retracted from the patient at 1308 shown in FIG. 13, for example, via a cannula.

Although in various exemplary embodiments, the surgical instrument can be operated as a hand-held device with various inputs to the transmission mechanism being provided manually, in an exemplary embodiment, the instrument 100 can be interfaced with a robotic surgical system, such as that shown in FIGS. 12A and 12B and as described above. In such an embodiment, the transmission mechanism may be configured as transmission mechanism 141 in FIGS. 14A and 14B, and the various described inputs can be received at the input disks 40 with the instrument disposed at a patient side console 1000 controlled via a central control console 3000 from signals received from a surgeon side console 2000. In addition, in an exemplary embodiment, to drive the cutting element, a voltage signal can be output from a controller, such as a separate instrument control box 3080 mounted or otherwise connected to a central control console 3000 or from a controller integrated therewith, and received via an onboard motor 5 disposed in the transmission mechanism 141. In various exemplary embodiments, inputs from the surgeon side console 2000 or from input units otherwise accessible to a surgeon can be provided to the controller(s) via various pedals 2010/2090 (e.g., to control cutting and fusing), and via hand-held grasping mechanisms 2020 (e.g., to control movement of the wrist 4 and instrument shaft 2). Those having ordinary skill in the art are familiar with the general use of such teleoperated robotic surgical systems to provide input from a surgeon at a surgeon side console to ultimately effect operation of a surgical instrument interfacing with a patient side console.

For exemplary configurations of gears, links, gimbal plates, levers, spring, rack and pinions, etc. that can be used in the transmission mechanism, as well as control algorithms that can be implemented (e.g., by various controllers associated with a central control console 3000) to control and transmit inputs received by the transmission mechanism 1 into torques and forces used to drive the various components of the end effector, reference is made to U.S. Provisional Patent Application No. 61/491,698, entitled "SURGICAL INSTRUMENT WITH MOTOR" (filed May 31, 2011); U.S.

Provisional Patent Application No. U.S. 61/491,671, entitled "SURGICAL INSTRUMENT WITH CONTROL FOR DETECTED FAULT CONDITION" (filed May 31, 2011); U.S. Provisional Patent Application No. U.S. 61/491,647, entitled "POSITIVE CONTROL OF ROBOTIC SURGICAL INSTRUMENT END EFFECTOR," (filed May 31, 2011); U.S. Provisional Application No. U.S. 61/491,804, entitled "GRIP FORCE CONTROL IN A ROBOTIC SURGICAL INSTRUMENT," (filed May 31, 2011); U.S. Provisional Application No. U.S. 61/491,798 and U.S. application Ser. No. 13/297,168, both entitled "DECOUPLING INSTRUMENT SHAFT ROLL AND END EFFECTOR ACTUATION IN A SURGICAL INSTRUMENT," (filed May 31, 2011 and Nov. 15, 2011, respectively); and U.S. Provisional Patent Application No. U.S. 61/491,821, entitled "SURGICAL INSTRUMENT WITH SINGLE DRIVE INPUT FOR TWO END EFFECTOR MECHANISMS," (filed May 31, 2011), all of which are incorporated by reference in their entireties herein, all of which are incorporated by reference in their entirety.

Figure 17:
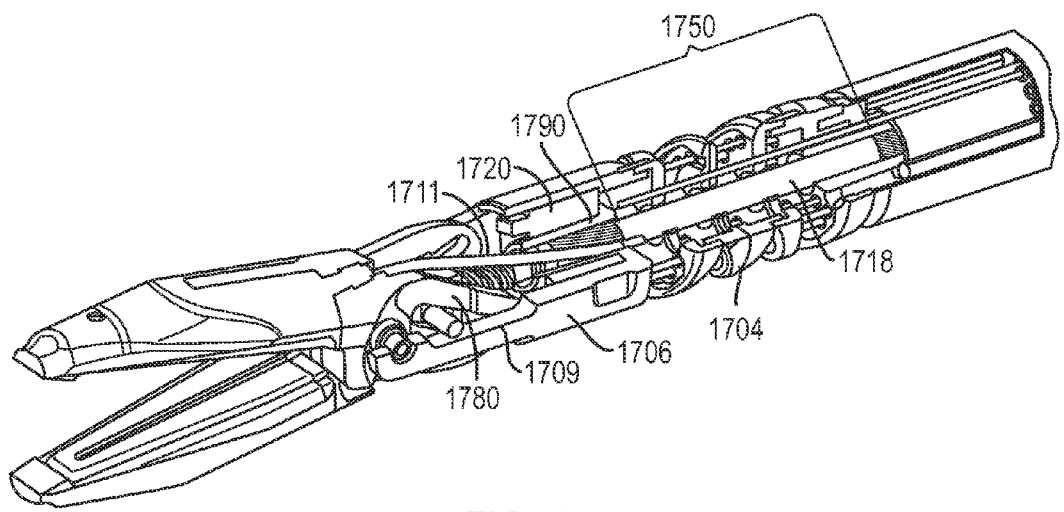
FIG. 17 is a partially cut-away perspective view of the end effector, wrist, and portion of the shaft of a fusing and cutting surgical instrument in accordance with an exemplary embodiment.
Figure 18:
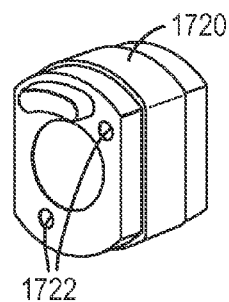
FIG. 18 is a perspective view of a cable routing plug in accordance with an exemplary embodiment.

FIG. 17 depicts a partially cutaway, perspective view of the wrist, end effector and a portion of the shaft an exemplary embodiment of a fusing and cutting surgical instrument in accordance with the present disclosure, with various components having differing structural configurations from other exemplary embodiments described above, as will be further explained below. In the exemplary embodiment of FIG. 17, the electrical conductors (one such electrical conductor 1711 being depicted), instead of having the slacked configuration as shown in FIG. 5 for example, are routed in a substantially straight configuration manner from the electrodes of the end effector. In an exemplary embodiment, as shown, the electrical conductors 17 can be routed in a substantially straight configuration through a molded plug 1720 (shown in isolation in FIG. 18) positioned in the clevis 1706. As shown in the detailed view of FIG. 18, the cable routing plug 1720 in an exemplary embodiment can be made of a molded plastic or rubber material that can route and hold the conductor cables 1711 in a tensioned manner through routing holes 1722. In this way, interference of the conductor cables 1711 with the movement of the surgical instrument, particularly the end effector movement, can be minimized. In various exemplary embodiments, the cable routing plug 1720 can be made of a material selected to increase friction between the conductor cables 1711 and the plug 1720 to the extent some movement of the cables 1711 through the routing holes 1722 occurs as a result of movement of the end effector. Exemplary materials that may be used for the plug 1720 include, but are not limited to, silicone, thermoplastic elastomers, and rubbers. As above, the electrical conductors 1711 can be routed through the holes 47 as they pass through the wrist 4, as shown in FIGS. 3 and 5.

The exemplary embodiment of FIG. 17 also illustrates a torque drive component with a portion of the outer surface of the outer winding layer removed, for example, via grinding (e.g., centerless grinding). As illustrated in the exemplary embodiment of FIG. 17, a portion 1750 that extends substantially along the wrist 1704 of the torque drive component 1718. Such removal of a portion of the outer surface of the outer layer of the torque drive component can provide a smoother outer surface, which in turn can result in increased flexibility of the torque drive component, enhance the consistency of the grip force, and/or increase the clearance between the torque drive component 1718 and the wrist 1704. In one exemplary embodiment, the outer layer of the torque drive component can be ground to about half of the thickness of the winding. For example, the outer winding layer may be ground to an outer diameter of the multi-layered tubular structure ranging from about 0.068 inches to about 0.070 inches.

Figure 19:
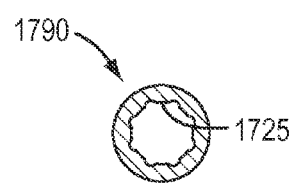
FIG. 19 is a cross-sectional view of an exemplary embodiment of a channel in the clevis of FIG. 17.

As also shown in FIG. 17, in an exemplary embodiment, a relief surface profile 1780 (the other relieve surface profile on the opposite side not visible in FIG. 17) can be provided on the surfaces of the cam extensions that abut the clevis ears 1709. Such a relief surface profile can provide a clearance between the two surfaces in order to reduce friction during the opening and closing of the jaws. Another surface that may include a surface profile in relief is the interior surface of the channel in the clevis through which the torque drive component passes. With reference to the exemplary embodiment of FIG. 17, and the cross-sectional view of FIG. 19, the channel 1790 through which the torque drive component 1718 passes in the clevis 1706 can be provided with a relief interior surface profile 1795 to assist in reducing friction between the torque drive component 1718 and the channel 1790.

Those having ordinary skill in the art will appreciate that the various component configurations described above with reference to FIG. 17-19 can be included in combination with any of the other exemplary embodiments described herein, including operational aspects.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present teachings. For example, various aspects have been described in the context of an instrument used in a surgical robotic system. But these aspects may be incorporated into hand-held instruments as well, with powered or hand-actuated actuation of the various degrees of freedom (e.g., shaft roll, wrist pitch and yaw, grip, knife).

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical instrument comprising:
   a shaft having a proximal end and a distal end, a longitudinal axis being defined between the proximal and distal ends;
   a wrist having a proximal end and a distal end, the proximal end of the wrist being coupled to the distal end of the shaft, the wrist being movable in pitch and yaw degrees of freedom, wherein the pitch degree of freedom is defined orthogonal to the longitudinal axis, and wherein the yaw degree of freedom is defined orthogonal to the longitudinal axis and to the pitch degree of freedom;

a surgical end effector coupled to the wrist, the surgical end effector comprising a jaw mechanism and a translating component, the translating component being movable lengthwise relative to the jaw mechanism;

a jaw mechanism drive element extending through the wrist and coupled to the jaw mechanism; and a translating component drive element extending through the wrist and coupled to the translating component of the surgical end effector, the translating component being configured to move lengthwise relative to the jaw mechanism in response to the translating component drive element translating along the longitudinal axis.

2. The surgical instrument of claim 1, further comprising:

a lead screw configured to rotate in response to force transmitted by the jaw mechanism drive element; and a drive nut configured to move along the lead screw in response to rotation of the lead screw, wherein movement of the drive nut along the lead screw moves the jaw mechanism between open and closed positions.

3. The surgical instrument of claim 2, wherein the jaw mechanism comprises a first jaw member and a second jaw member opposing the first jaw member, the first jaw member comprising a cam extension having a cam slot that receives a portion of the drive nut.

4. The surgical instrument of claim 1, the jaw mechanism being configured to move between open and closed positions in response to rotation of the jaw mechanism drive element.

5. The surgical instrument of claim 4, wherein the jaw mechanism drive component comprises a torque tube having multiple concentric winding layers.

6. The surgical instrument of claim 5, wherein the multiple concentric winding layers comprise at least two winding layers, the at least two winding layers having opposite winding directions.

7. The surgical instrument of claim 5, wherein the multiple concentric winding layers comprise an inner winding layer, an outer winding layer, and a middle winding layer between the inner winding layer and the outer winding layer each of the inner and outer winding layers having a first winding direction, and the middle winding layer having a second winding direction opposite to the first direction.

8. The surgical instrument of claim 5, wherein the jaw mechanism drive component comprises a lead screw and a drive nut configured to move along the lead screw in response to rotation of the lead screw, wherein the torque tube extends through the wrist and has a distal end coupled to the lead screw, and wherein the drive nut is engaged with the jaw mechanism to open and close the jaw mechanism in response to movement of the drive nut along the lead screw.

9. The surgical instrument of claim 1, further comprising a transmission mechanism at a proximal portion of the surgical instrument, the transmission mechanism being configured to receive one or more inputs and, in response to receiving the one or more inputs, transmit force to translate the translating component drive element and transmit torque to rotate the jaw mechanism drive element.

10. The surgical instrument of claim 1, wherein the translating component drive element is flexible in the pitch and yaw degrees of freedom at least at the wrist.

11. The surgical instrument of claim 10, wherein the translating component drive element comprises a cable.

12. The surgical instrument of claim 1, wherein the translating component drive element extends through a center lumen of the shaft and the wrist from the proximal end of the shaft to the end effector.

13. The surgical instrument of claim 1, wherein the jaw mechanism comprises an electrode configured to deliver energy sufficient to fuse tissue.

14. The surgical instrument of claim 13, wherein the jaw mechanism is configured to grip tissue in a closed position with a sufficient pressure to permit fusing of the tissue during delivery of the energy in the closed position.

15. The surgical instrument of claim 1, wherein the translating component drive element includes a wire.

16. The surgical instrument of claim 1, wherein the translating component comprises a blade.

17. The surgical instrument of claim 1, wherein the jaw mechanism drive element comprises a torque tube, and the translating component drive element comprises a cable extending through the torque tube.

18. The surgical instrument of claim 1, wherein the surgical instrument is configured to interface with a patient side cart of a teleoperated surgical system.

19. The surgical instrument of claim 1, wherein the jaw mechanism is configured to exert a grip force ranging from about 4.25 lbs to about 8.75 lbs throughout a range of wrist articulation of +/−60 degrees in each of the pitch and yaw degrees of freedom.

20. The method of claim 1, further comprising a transmission mechanism at a proximal portion of the surgical instrument, the transmission mechanism being configured to transmit force along the shaft to move the wrist in at least one of the pitch and yaw degrees of freedom.

21. A method of operating a surgical instrument, the method comprising:

transmitting a first force from a transmission mechanism disposed at a proximal portion of a shaft of the surgical instrument to articulate a wrist of the surgical instrument coupled to a distal end of the shaft, the wrist being articulatable in pitch and yaw degrees of freedom, wherein the pitch degree of freedom is defined orthogonal to a longitudinal axis of the shaft, and wherein the yaw degree of freedom is defined orthogonal to the longitudinal axis and to the pitch degree freedom;

transmitting a second force from the transmission mechanism to a jaw mechanism drive element coupled to move a jaw mechanism of an end effector supported by the wrist, the jaw mechanism closing in response to the second force; and transmitting a third force from the transmission mechanism to a translating component drive element coupled to a translating component of the end effector, the translating component moving lengthwise relative to the jaw mechanism in response to the third force.

22. The method of claim 21, wherein transmitting the second force comprises transmitting a torque to the jaw mechanism drive element to rotate the jaw mechanism drive element.

23. The method of claim 21, wherein transmitting the third force comprises transmitting a push force or a pull force to the translating component drive element.

24. The method of claim 21, wherein the jaw mechanism extends in a distal direction away from a distal end of the wrist, and wherein moving the translating component comprises moving the translating component between relatively proximal and distal positions along the jaw mechanism.

25. The method of claim 21, wherein the jaw mechanism comprises a first jaw and a second jaw opposing the first jaw, and wherein moving the translating component comprises moving the translating component between the first and second jaws.

26. The method of claim 21, further comprising conducting electrical energy between jaws of the jaw mechanism in the closed position of the jaw mechanism, the electrical energy being sufficient to fuse tissue gripped by the jaw mechanism in the closed position.

27. The method of claim 21, wherein the translating component drive element extends through the wrist of the surgical instrument.

\* \* \* \* \*